United States Patent
Moghaddam et al.

(10) Patent No.: US 9,179,843 B2
(45) Date of Patent: Nov. 10, 2015

(54) METHOD AND SYSTEM FOR OPTICALLY EVALUATING PROXIMITY TO THE INFERIOR ALVEOLAR NERVE IN SITU

(75) Inventors: Hassan Ghaderi Moghaddam, Ottawa (CA); Pascal Gallant, Québec (CA); Ozzy Mermut, Québec (CA); Israël Veilleux, Sainte-Rose-de-Watford (CA)

(73) Assignee: Hassan Ghaderi Moghaddam, Ottawa, Ontario (CA)

( * ) Notice: Subject to any disclaimer, the term of this patent is extended or adjusted under 35 U.S.C. 154(b) by 203 days.

(21) Appl. No.: 13/329,557

(22) Filed: Dec. 19, 2011

(65) Prior Publication Data
US 2012/0271176 A1 Oct. 25, 2012

Related U.S. Application Data

(60) Provisional application No. 61/477,787, filed on Apr. 21, 2011.

(51) Int. Cl.
*A61B 6/00* (2006.01)
*A61B 5/00* (2006.01)
(Continued)

(52) U.S. Cl.
CPC ............. *A61B 5/0075* (2013.01); *A61B 5/4542* (2013.01); *A61B 5/489* (2013.01); *A61B 5/4893* (2013.01); *A61C 19/04* (2013.01); *A61B 5/14551* (2013.01)

(58) Field of Classification Search
CPC ...... A61C 19/04; A61B 5/489; A61B 5/4893; A61B 5/14551
USPC ............. 356/327, 479, 497; 378/22; 433/173, 433/29; 600/407, 473; 850/6
See application file for complete search history.

(56) References Cited

U.S. PATENT DOCUMENTS

| 4,887,606 A | 12/1989 | Yock et al. |
| 5,006,984 A | 4/1991 | Steele |

(Continued)

FOREIGN PATENT DOCUMENTS

| CA | 1305246 | 7/1992 |
| CA | 2544585 | 5/2005 |

(Continued)

OTHER PUBLICATIONS

Micro-Optics Assembly in Dental Drill as a platform for imaging and sensing suring the surgical drilling, Dedy et al, IEEE Conference, Nov. 2010.*

(Continued)

*Primary Examiner* — Amanda Lauritzen Moher
*Assistant Examiner* — Serkan Akar
(74) *Attorney, Agent, or Firm* — Dawn-Marie Bey; Bey & Cotropia PLLC

(57) ABSTRACT

A low coherence interferometry probe system for evaluating proximity to a tissue layer, comprising a low coherence light source, an excitation optical fiber to bring the low coherence excitation light near the tissue layer and a collection optical fiber for capturing back-scattered light from the tissue layer. The probe system comprises an interferometry sub-system and a processor for evaluating a distance to the tissue layer. There is also provided a spectral absorption probe system for evaluating proximity to an artery, comprising a light source excitation light having a wavelength adapted for absorption by blood chromophores, an excitation optical fiber and a collection optical fiber. The probe system comprises a light detector and a processor for determining a distance to the artery using the Beer-Lambert law of light absorption with a value for surrounding tissue attenuation coefficient ($\mu\text{eff}$). A probe system combining low coherence interferometry and spectral absorption is also provided.

23 Claims, 18 Drawing Sheets

(51) Int. Cl.
*A61C 19/04* (2006.01)
*A61B 5/1455* (2006.01)

(56) References Cited

U.S. PATENT DOCUMENTS

| | | | |
|---|---|---|---|
| 5,078,147 A | 1/1992 | Reid et al. | |
| 5,080,103 A | 1/1992 | Olivier | |
| 5,112,224 A | 5/1992 | Shirota et al. | |
| 5,115,813 A | 5/1992 | Ylander et al. | |
| 5,131,395 A | 7/1992 | Gehlbach | |
| 5,200,604 A | 4/1993 | Rudko et al. | |
| 5,309,915 A | 5/1994 | Ember | |
| 5,320,529 A | 6/1994 | Pompa | |
| 5,402,781 A | 4/1995 | Dimarogonas | |
| 5,423,321 A | 6/1995 | Fontenot et al. | |
| 5,428,223 A | 6/1995 | Jatteau et al. | |
| 5,518,008 A | 5/1996 | Cucchiaro et al. | |
| 5,564,423 A | 10/1996 | Mele et al. | |
| 5,651,363 A | 7/1997 | Kaufman et al. | |
| 5,678,555 A | 10/1997 | O'Connell et al. | |
| 5,688,118 A | 11/1997 | Hayka et al. | |
| 5,772,594 A | 6/1998 | Barrick | |
| 5,795,295 A | 8/1998 | Hellmuth et al. | |
| 5,842,149 A | 11/1998 | Harrell et al. | |
| 5,850,184 A | 12/1998 | Bailey et al. | |
| 5,896,102 A | 4/1999 | Heger | |
| 5,917,314 A | 6/1999 | Heger et al. | |
| 6,023,159 A | 2/2000 | Heger | |
| 6,030,221 A | 2/2000 | Jones et al. | |
| 6,074,394 A | 6/2000 | Krause | |
| 6,109,270 A | 8/2000 | Mah et al. | |
| 6,134,003 A | 10/2000 | Tearney et al. | |
| 6,419,484 B1* | 7/2002 | DaSilva et al. | 433/29 |
| 6,451,009 B1 | 9/2002 | Dasilva et al. | |
| 6,466,817 B1 | 10/2002 | Kaula et al. | |
| 6,485,413 B1 | 11/2002 | Boppart et al. | |
| 6,491,522 B1 | 12/2002 | Jensen et al. | |
| 6,503,249 B1 | 1/2003 | Krause | |
| 6,517,487 B1 | 2/2003 | Mazess et al. | |
| 6,564,087 B1 | 5/2003 | Pitris et al. | |
| 6,597,941 B2 | 7/2003 | Fontenot et al. | |
| 6,620,101 B2 | 9/2003 | Azzam et al. | |
| 6,626,837 B2 | 9/2003 | Muramatsu et al. | |
| 6,665,948 B1 | 12/2003 | Kozin et al. | |
| 6,675,033 B1 | 1/2004 | Lardo et al. | |
| 6,702,746 B1 | 3/2004 | Srouji | |
| 6,704,439 B1 | 3/2004 | Lee et al. | |
| 6,718,196 B1 | 4/2004 | Mah et al. | |
| 6,736,508 B2 | 5/2004 | Xie et al. | |
| 6,889,075 B2* | 5/2005 | Marchitto et al. | 600/473 |
| 7,066,278 B2 | 6/2006 | Shotey | |
| 7,074,187 B2 | 7/2006 | Selzer et al. | |
| 7,079,883 B2 | 7/2006 | Marino et al. | |
| 7,148,970 B2 | 12/2006 | de Boer et al. | |
| 7,177,677 B2 | 2/2007 | Kaula et al. | |
| 7,203,351 B1 | 4/2007 | Swindale et al. | |
| 7,231,243 B2 | 6/2007 | Tearney et al. | |
| 7,239,909 B2 | 7/2007 | Zeman et al. | |
| 7,267,546 B2 | 9/2007 | Scott et al. | |
| 7,285,093 B2 | 10/2007 | Anisimov et al. | |
| 7,307,734 B2* | 12/2007 | Dogariu | 356/497 |
| 7,310,150 B2 | 12/2007 | Guillermo et al. | |
| 7,319,639 B2 | 1/2008 | Heyman | |
| 7,366,376 B2 | 4/2008 | Shishkov et al. | |
| 7,382,686 B2 | 6/2008 | Innes | |
| 7,383,163 B2 | 6/2008 | Holberg et al. | |
| 7,385,483 B2 | 6/2008 | Lee | |
| 7,407,566 B2 | 8/2008 | Jiang et al. | |
| 7,411,517 B2 | 8/2008 | Flanagan | |
| 7,424,142 B2 | 9/2008 | Arnold et al. | |
| 7,447,408 B2 | 11/2008 | Bouma et al. | |
| 7,457,443 B2 | 11/2008 | Persky | |
| 7,470,236 B1 | 12/2008 | Kelleher et al. | |
| 7,503,896 B2 | 3/2009 | Miele et al. | |
| 7,510,536 B2 | 3/2009 | Foley et al. | |
| 7,522,953 B2 | 4/2009 | Kaula et al. | |
| 7,582,058 B1 | 9/2009 | Miles et al. | |
| 7,602,184 B2 | 10/2009 | Du et al. | |
| 7,630,083 B2 | 12/2009 | de Boer et al. | |
| 7,643,152 B2 | 1/2010 | de Boer et al. | |
| 7,643,153 B2 | 1/2010 | de Boer et al. | |
| 7,657,308 B2 | 2/2010 | Miles et al. | |
| 7,664,544 B2 | 2/2010 | Miles et al. | |
| 7,676,023 B2 | 3/2010 | Lang et al. | |
| 7,691,057 B2 | 4/2010 | Miles et al. | |
| 7,725,169 B2* | 5/2010 | Boppart et al. | 600/473 |
| 7,733,497 B2 | 6/2010 | Yun et al. | |
| 7,758,342 B2 | 7/2010 | Lewallen et al. | |
| 7,761,139 B2 | 7/2010 | Tearney et al. | |
| 2001/0047137 A1 | 11/2001 | Moreno et al. | |
| 2002/0016533 A1* | 2/2002 | Marchitto et al. | 600/310 |
| 2002/0045828 A1 | 4/2002 | Skidmore et al. | |
| 2003/0009111 A1 | 1/2003 | Cory et al. | |
| 2003/0069509 A1* | 4/2003 | Matzinger et al. | 600/504 |
| 2005/0038343 A1 | 2/2005 | Cao et al. | |
| 2005/0101866 A1 | 5/2005 | Goodwin et al. | |
| 2005/0142517 A1* | 6/2005 | Frysh et al. | 433/173 |
| 2005/0143662 A1* | 6/2005 | Marchitto et al. | 600/473 |
| 2005/0151976 A1* | 7/2005 | Toma | 356/497 |
| 2005/0190372 A1* | 9/2005 | Dogariu | 356/479 |
| 2006/0013544 A1* | 1/2006 | Bouma et al. | 385/116 |
| 2006/0015041 A1 | 1/2006 | Neal et al. | |
| 2006/0079781 A1 | 4/2006 | Germond-Rouet et al. | |
| 2006/0239532 A1 | 10/2006 | Taguchi et al. | |
| 2006/0285635 A1* | 12/2006 | Boppart et al. | 378/22 |
| 2007/0025607 A1 | 2/2007 | Takaishi et al. | |
| 2007/0038040 A1 | 2/2007 | Cense et al. | |
| 2007/0100212 A1 | 5/2007 | Pimenta et al. | |
| 2007/0122345 A1 | 5/2007 | Golijanin | |
| 2007/0167710 A1 | 7/2007 | Unal et al. | |
| 2007/0167717 A1 | 7/2007 | James et al. | |
| 2007/0286467 A1 | 12/2007 | Asano et al. | |
| 2008/0033569 A1 | 2/2008 | Ferren et al. | |
| 2008/0253521 A1 | 10/2008 | Boyden et al. | |
| 2008/0253523 A1 | 10/2008 | Boyden et al. | |
| 2008/0253528 A1 | 10/2008 | Boyden et al. | |
| 2008/0253531 A1 | 10/2008 | Boyden et al. | |
| 2008/0253627 A1 | 10/2008 | Boyden et al. | |
| 2009/0053666 A1 | 2/2009 | Buchanan et al. | |
| 2009/0108205 A1 | 4/2009 | Duffy et al. | |
| 2009/0142726 A1 | 6/2009 | Gamba et al. | |
| 2009/0171205 A1 | 7/2009 | Kharin et al. | |
| 2009/0281412 A1 | 11/2009 | Boyden et al. | |
| 2009/0281413 A1 | 11/2009 | Boyden et al. | |
| 2009/0287076 A1 | 11/2009 | Boyden et al. | |
| 2009/0292195 A1 | 11/2009 | Boyden et al. | |
| 2009/0296887 A1 | 12/2009 | Boyden et al. | |
| 2009/0306487 A1* | 12/2009 | Crowe et al. | 600/322 |
| 2010/0010367 A1 | 1/2010 | Foley et al. | |
| 2010/0056922 A1 | 3/2010 | Florent et al. | |
| 2010/0160764 A1* | 6/2010 | Steinberg et al. | 600/407 |
| 2010/0218286 A1* | 8/2010 | Lai et al. | 850/6 |
| 2010/0280392 A1* | 11/2010 | Liu et al. | 600/475 |
| 2011/0090499 A1* | 4/2011 | Van Der Mark | 356/327 |
| 2014/0058226 A1* | 2/2014 | Chernobrod et al. | 600/316 |

FOREIGN PATENT DOCUMENTS

| | | | |
|---|---|---|---|
| CA | 2580720 | 3/2006 | |
| CA | WO 2009/036561 A1 * | 3/2009 | A61B 6/00 |
| EP | 0683643 | 11/1995 | |
| EP | 0757784 | 2/1997 | |
| EP | 1741394 | 1/2007 | |
| EP | 1743591 | 1/2007 | |
| NL | WO2007006698 | * 1/2007 | |
| RU | 2370225 | 10/2009 | |
| WO | 03103484 | 12/2003 | |

(56) References Cited

FOREIGN PATENT DOCUMENTS

| WO | 2005074831 | 8/2005 |
|---|---|---|
| WO | 2007006698 | 1/2007 |
| WO | 2008126560 | 10/2008 |

OTHER PUBLICATIONS

Mustufa, An image based robotic assistance for microsurgery of the inner ear, Retrieved on Jul. 29, 2010 from: http://citeseerx.ist.psu.edu/viewdoc/download?doi=10.1.1.127.1199&rep=rep1&type=pdf, Sep. 2005.

Juodzbalys G, Wang HL. Guidelines for the Identification of the Mandibular Vital Structures: Practical Clinical Applications of Anatomy and Radiological Examination Methods. J Oral Maxillofac Res 2010 (Apr.-Jun.);1(2):e1 URL: http://www.ejomr.org/JOMR/archives/2010/2/e1/e1ht.pdf—doi:10.5037/jomr.2010.1201.

Tischler. In-Office Cone Beam Computerized Tomography: Technology Review and Clinical Examples. Retrieved on Jul. 29, 2010 from: http://s3.amazonaws.com/webgen_einsteinwebsites/public/assets/6485/ In_Office_CBCT_Dent_Today_6-08.pdf.

Misch et al, "Mandibular Nerve Neurosensory Impairment After Dental Implant Surgery: Management and Protocol", Implant Dentistry, 2010, vol. 19, No. 5, Lippincott Williams & Wilkins, pp. 378-386.

C.D. Morris et al., The Anatomic Basis of Lingual Nerve Trauma Associated With Inferior Alveolar Block Injections, 2010 American Association of Oral and Maxillofacial Surgeons, J Oral Maxillofac Surg 68, pp. 2833-2836, Dallas, TX.

Ong, F.R., Bouazza-Marouf, K.; 1999; The detection of drill bit break-through for the enhancement of safety in mechatronic assisted orthopaedic drilling; Mechatronics 9 : 565-588.

A. Mariampillai et al., Speckle variance detection of microvasculature using swept-source optical coherence tomography, Optics Letters, vol. 33, No. 13, 2008, pp. 1530-1532, Canada.

A. Mariampillai et al., "Optimized speckle variance OCT imaging of microvasculature", Optics Letters, vol. 35, No. 8, 2010, pp. 1257-1259, Canada.

D. Contini et al. "Photon migration through a turbid slab described by a model based on diffusion approximation I—Theory", Appl. Opt. 36(19), p. 4587, 1997.

Humphries C., Nerves Light Up to Warn Surgeons Away, Retrived on Feb. 14, 2011 from: www.technologyreview.com/read_article.aspx?id=32325&a=f.

Augustin, G., Davila, S., Mihoci, K., Udiljak, T., Vedrina, D.S., Antabak, A. 2008 Thermal osteonecrosis and bone drilling parameters revisited Archives Of Orthopaedic And Trauma Surgery 128: 71-77 Times Cited : 0 (Univ Hosp Ctr Zagreb, Dept Surg, Kispaticeva 12, Zagreb 10000, Croatia).

Carter R.B, and Keen E.N. 1971 Intramandibular Course of Inferior Alveolar Nerve Journal Of Anatomy 108: 433-440 Times Cited : 72 (Cambridge Univ Press, 40 West 20th Street, New York, NY 10011-4211).

Degidi, M., Piattelli, A., Iezzi, G., Carinci, F. 2007 Do longer implants improve clinical outcome in immediate loading? International Journal Of Oral And Maxillofacial Surgery 36 : 1172-1176 Times Cited : 0 (Univ G dAnnunzio, Sch Dent, Via F Sciucchi 63, I-66100 Chieti, Italy).

Esposito M, Hirsch JM, Lekholm U, Thomsen P. 1998 Biological factors contributing to failures of osseointegrated oral implants (I). Success criteria and epidemiology European Journal of Oral Sciences 106 : 527-551 Times Cited : 233 (Gothenburg Univ, Inst Anat & Cell Biol, Med Gatan 3, S-41390 Gothenburg, Sweden).

Kondo T, Ong SH, Foong KWC 2004 Computer-based extraction of the inferior alveolar nerve canal in 3-D space Computer Methods And Programs In Biomedicine 76 : 181-191 Times Cited : 1 (Natl Univ Singapore, Dept Elect & Comp Engn, Singapore 0511, Singapore).

Mardinger, O., Chaushu, G., Arensburg, B., Taicher, S., Kaffe, I. 2000 Anatomic and radiologic course of the mandibular incisive canal Surgical and Radiologic Anatomy 22 : 157-161 Times Cited : 5 (Sapir Med Ctr, Dept Oral & Maxillofacial Surg, Kfar Saba, Israel ).

Renouard F., Nisand, D. 2006 Impact of implant length and diameter on survival rates Clinical Oral Implants Research 17 : 35-51 Suppl. 2 Times Cited : 10 (Univ Paris 07, Dept Periodontol, Paris, France).

Wadu, S.G., Penhall, B., Townsend, G.C. 1997 Morphological variability of the human inferior alveolar nerve Clinical Anatomy 10 : 82-87.

Wiggins, K.L., Malkin, S. 1976 Drilling Of Bone Journal of Biomechanics 9 : 553-559 Published : 1976 Times Cited : 29 (Coll Petr & Minerals, Dept Appl Mech Engn, Dhahran, Saudi Arabia And Suny Buffalo, Dept Mech Engn, Buffalo, NY 14214 USA).

Zoud, K., Doran, G.A. 1993 Microsurgical Anatomy Of The Inferior Alveolar Neurovascular Plexus Surgical And Radiologic Anatomy 15 : 175-179 Times Cited : 7 (Univ Sydney, Dept Anat, Sydney, NSW 2006 Australia ).

P.A. Öberg, T. Sundqvist, A. Johansson, M. Sundberg, "Characterisation of the cartilage/bone interface utilizing reflectance spectroscopy", US Army report, Oct. 25, 2001, 3 pages.

Margallo Balbás, Eduardo, "Optical Techniques for the study of living tissue", PhD Thesis, Technische Universtiteit Delft, 2010, 205 pages.

L. Choël et al., "Trabecular alveolar bone microarchitecture in the human mandible using high resolution magnetic resonance imaging", Dentomaxillofacial Radiology 33, 2004, pp. 177-182, The British Institute of Radiology.

M. Firbank, M. Hiraoka, M. essenpreis, D.T. Delpy, "Measurement of the optical properties of the skull in the wavelength range 650-950 nm", Phys. Med. Biol. 38, 1993, pp. 503-510.

N. Ugryumova, S.J. Matcher, D. P. Attenburrow, "Measurement of bone mineral density via light scattering", Phys. Med. Biol. 49, 2004, pp. 469-483.

"Optical coherence tomography" from Wikipedia, the free encyclopedia, retrieved on Oct. 29, 2014 from http://en.wikipedia.org/wiki/Optical_coherence_tomography, 14 pages.

"Absorption spectroscopy" from Wikipedia, the free encyclopedia, retrieved on Oct. 29, 2014 from http://en.wikipedia.org/wiki/Absorption_spectroscopy, 9 pages.

"Near-infrared spectroscopy" from Wikipedia, the free encyclopedia, retrieved on Oct. 29, 2014 from http://en.wikipedia.org/wiki/Near-infrared_spectroscopy, 7 pages.

V. Chan, S. Underwood, "A single-chip pulsoximeter design using the MSP430", Texas Instrument White paper #SLA274, Nov. 2005, 10 pages.

N. Townsend, M. Term, "Pulse Oximetry", Medical Electronics, 2002, p. 32-42.

J. Bachiochi, "Light-to-frequency conversion (Part 1): TSL230R-Based pulse oximeter", Circuit Cellar 173, Dec. 2004, p. 26-31.

Y.T. Li, "Pulse Oximetry", white paper, Dept. of Electronic Engineering, University of Surrey, www.surrey.ac.uk, 5 pages, Dec. 2004.

E. Trosman, E. Palatnik, "Pulse Oximeter uses ADuC7024 microconverter", Analogue Dialogue, Analog devices Inc., 4 pages, www.analog.com/library/analoguedialogue/archives/41-01/ pulse_oximeter.html, Jan. 1998.

C. Kasseck, M. Kratz, A. Torcasio, N.C. Gerhardt, G. H. Van Lenthe, T. Gambichler, K. Hoffmann, D.B. Jones, M.R. Hoffmann, "Comparison of optical coherence tomography, microcomputed tomography and histology at a three-dimensionally imaged trabecular bone sample", J. Biomed., 2010, pp. 1-6, Opt. 15(4), 046019.

A. Mariampillai, B.A. Standish, E.H. Moriyama, M. Khurana, N.R. Munce, M.K.K. Leung, J. Jiang, A. Cable, B.C. Wilson, I. A. Vitkin, V.X.D, Yang, "Speckle variance detection of microvasculature using swept-source optical coherence tomography", Optic Letters, 2008, pp. 1530-1532, 33(13).

A. Mariampillai, M.K.K. Leung, M. Jarvi, B.A. Standish, K. Lee, B.C. Wilson, A. Vitkin, V.X.D. Yang, "Optimized speckle variance OCT imaging of microvasculature", Optic Letters, 2010, pp. 1257-1259, 35(8).

R.K. Wang, L. An, "Doppler optical micro-angiography for volumetric imaging of vascular perfusion in vivo", Optics Express, 2009, pp. 8926-8940, 17(11).

(56) References Cited

OTHER PUBLICATIONS

R.K. Wang, L. An, P. Francis, D.J. Wison, "Depth-resolved imaging of capillary networks in retina and choroid using ultrahigh sensitive optical microangiography", Optic Letters, 2010, pp. 1467-1469, 35(9).

B.E. Bouma, L.E. Nelson, G.J. Tearney, D.J. Jones, M.E. Brezinski, J.G. Fujimoto, "Optical coherence tomographic imaging of human tissue at 1.55 pm and 1.81 µm using Er- and Tm-doped fiber sources", Journal of Biomedical Optics, 1998, pp. 76-79, Opt. 3(1).

P.J.L. Webster, B.Y.C. Leung, V.X.D. Yang, J.M. Fraser, "Guidance of hard tissue ablation by forward-viewing optical coherence tomography", Proc. SPIE 7554, Optical Coherence Tomography and Coherence Domain Optical Methods in Biomedicine XIV, J.A. Izatt, J.G. Fujimoto, V.V. Tuchin Eds., 2010, pp. 1-6 75540Z.

N.M. Fried, S. Rais-Bahrami, G.A. Lagoda, A.Y. Chuang, L.M. Su, A.L. Burnett III, "Identification and imaging of the nerves responsible for erectile function in rat prostate, in vivo, using optical nerve stimulation and optical coherence tomography", IEEE Journal of Selected Topics in Quantum Electronics, 2007, pp. 1641-1645, 13(6).

E. Margallo-Balbas, P.J. French, P.A. Wieringa, "Light transport in trabecular bone: Monte Carlo simulation based on 3D triangle meshes", Proc. SPIE 6142, Medical Imaging 2006: Physics of Medical Imaging, M.J. Flynn, J. Hsieh Eds., 2006, pp. 1-12, 61421K.

Y.C. Tao, D. Fried, "Near-infrared image-guided laser ablation of dental decay", Journal of Biomedical Optics, 2009, pp. 1-6, 14(5), 054045.

J. Sakamoto, T. Higaki, S. Okamoto, T. Kamio, M. Otonari-Yamamoto, K. Nishikawa, T. Sano, "Optimum conditions for detecting the inferior alveolar artery using phase-contrast magnetic resonance angiography", Oral Radiol., 2010, 9-15, 26.

\* cited by examiner

METHOD AND SYSTEM FOR OPTICALLY EVALUATING PROXIMITY TO THE INFERIOR ALVEOLAR NERVE IN SITU

CROSS REFERENCE TO RELATED APPLICATION

This application claims priority of U.S. Provisional Patent Application Ser. No. 61/477,787 filed on Apr. 21, 2011 and entitled "METHOD AND SYSTEM FOR OPTICALLY EVALUATING PROXIMITY TO THE INFERIOR ALVEOLAR NERVE IN SITU", the specification of which is hereby incorporated by reference.

TECHNICAL FIELD

The invention relates to methods and systems for evaluating proximity to a target, more specifically, for evaluating proximity to a nerve.

BACKGROUND OF THE ART

Dental implants are a widely accepted treatment for the partially or completely edentulous patient. Dental implants are the fastest growing procedure in dentistry today. It is a 1 billion dollar industry in the USA. Dental implants offer a suitable alternative to mucosal adhering dentures and allow a more natural option for the patient. Implants have a high success rate when given proper care and when post-surgical instructions are followed. Dental implants can be in the form of a single tooth replacement, or can replace a series or an entire set of teeth. The basic implant procedure involves drilling a channel in the mandible where an artificial root is surgically inserted. A dental prosthesis is then placed onto the frame of the artificial root. Within a few months of recovery, the patient should have a fully integrated and functional prosthesis.

Implant procedures are not without complications. The goal of an implant procedure is to attain a successful level of osseointegration. Osseointegration is defined as the direct anchorage of an implant by the formation of bony tissue around the implant without the growth of fibrous tissue at the bone-implant interface. Implants surrounded with fibrous tissue show mobility when a load is applied. The successfully osseointegrated implant shows no mobility when loaded. Other major factors for the successful implant depend mainly on the type of jaw treated, the density of the bone, and the length of the implant. Implant length is the depth created by the surgeon upon drilling a channel in the mandible. Short implants have a length of less than 10 mm and are noted to have larger failure rates. Hence the need to create sufficient length for successful osseointegration of implants within the mandible is a priority.

However, the drilling of a large implant channel within the mandible carries a risk of breaching an intraosseous canal which encloses the inferior alveolar nerve (IAN). Disruption of the IAN can lead to loss of sensation in the anterior mandible area, such as paresthesia or numbness to the lower lip, due to the disruption of the mental nerve, which is the terminal branch of the IAN and is the neural bundle serving this area. The loss of sensation for the patient is certainly undesirable.

The reported incidence of nerve injury from implant placement in the literature is highly variable and ranges depending on the study from 0% to as high as 44% (Misch and Resnik Implant Dentistry 2010; 19:378-386). A survey at the Misch international institute indicated that 73% of dentists have encountered neurosensory impairment within their practice. To help prevent nerve injury, patients can be subjected to CT scans which are costly and also involve radiation. The standard error for a CT scan is still in the range of 1.7 mm. This measurement error can result in nerve damage.

There is thus a need to develop a surgical drill which is able to detect the proximity and/or location of the IAN in the mandible, preferably during implant procedures. The sensor device should allow the drill to approach closely, but not impair or damage the IAN within an acceptable error limit of the intraosseous canal. Hence, a system that automatically terminates drill action when in close range of the IAN would be most desirable.

SUMMARY

According to one broad aspect of the present invention, there is provided a spectral absorption probe system for evaluating proximity to an artery, comprising a light source for generating excitation light having a wavelength adapted for absorption by blood chromophores, an excitation optical fiber to bring the excitation light near the artery and a collection optical fiber for capturing back-scattered light from the artery. The spectral absorption probe system comprises a light detector operatively connected to the collection optical fiber and a signal processor operatively connected to the light detector for determining a distance to the artery based on the back-scattered light and on Beer-Lambert law of light absorption using a value for surrounding tissue attenuation coefficient ($\mu$eff).

In one embodiment, the spectral absorption probe system further comprises a biocompatible metallic rod surrounding the excitation optical fiber and the collection optical fiber.

In one embodiment, the excitation optical fiber and the collection optical fiber are provided in a single double-clad optical fiber with a fiber core of the double-clad optical fiber bringing the excitation light near the artery and a first clad of the double-clad optical fiber capturing the back-scattered light from the artery.

In one embodiment, the probe system is fibered and integrated within a hollow core of a drill bit.

In one embodiment, an operating depth range of the probe system is comprised between 1 mm and 5 mm.

In one embodiment, the light source is selected from a group consisting of a LED, a laser and a set of light source units.

In a further embodiment, the wavelength of the light source is comprised between 650 nm and 900 nm.

In one embodiment, the spectral absorption probe system further comprises an additional light source having a wavelength adapted for absorption by blood chromophores, the wavelengths of the light source and of the additional light source being each comprised between 650 nm and 900 nm.

In one embodiment, the light detector is selected from a group consisting of a photodiode, an avalanche photodiode (APD), a photomultiplier tube (PMT) and a camera.

In one embodiment, the spectral absorption probe system further comprises a calibration unit having a pulse oxymeter for monitoring oxygen saturation levels to maintain an inline calibration of arterial blood absorption properties.

In one embodiment, the surrounding tissue attenuation coefficient ($\mu$eff) is determined according to absorption and scattering in surrounding tissue of a calibration excitation signal.

In one embodiment, the signal processor comprises a lock-in amplifier and a heterodyning processing circuit connected thereto.

In one embodiment, the light detector is AC-coupled to the signal processor.

In another embodiment, the excitation optical fiber and the collection optical fiber are separated from each other and extend angularly.

In a further embodiment, a single one of the excitation optical fiber and the collection optical fiber is integrated within a hollow core of a drill bit.

According to another broad aspect of the present invention, there is provided a low coherence interferometry probe system for evaluating proximity to a tissue layer, comprising a low coherence light source for generating low coherence excitation light, an excitation optical fiber to bring the low coherence excitation light near the tissue layer and a collection optical fiber for capturing back-scattered light from the tissue layer. The low coherence interferometry probe system comprises a low coherence interferometry sub-system operatively connected to the excitation optical fiber and the collection optical fiber and having a beam splitter and a reference mirror. The low coherence interferometry probe system comprises a digital signal processor operatively connected to the low coherence interferometry sub-system for evaluating a distance to the tissue layer based on the back-scattered light received by the collection optical fiber.

In one embodiment, the tissue layer is selected from a group consisting of a canal wall, an artery, a nerve, a neurovascular bundle and a sinus floor.

In one embodiment, the probe system is fibered and integrated within a hollow core of a drill bit.

In one embodiment, the low coherence light source is selected from a group consisting of a superluminescent LED, a pulsed laser and a frequency-swept laser source.

In one embodiment, an operating depth range of the probe system is comprised between 1 mm and 5 mm.

In one embodiment, the excitation optical fiber and the collection optical fiber are both embedded in a single-mode optical fiber.

In another embodiment, the excitation optical fiber and the collection optical fiber are provided in a single double-clad optical fiber having a core acting as an excitation channel, an inner clad acting as a collection channel and an outer clad surrounding the inner cladding.

In one embodiment, the probe system is operated in A-mode.

In another embodiment, the probe system comprises a forward-looking transverse scanner enabling B-mode imaging.

In a further embodiment, the excitation optical fiber and the collection optical fiber are both embedded in a rotating beveled double-clad optical fiber having a core acting as an excitation channel, an inner cladding acting as a collection channel and an outer cladding surrounding the inner cladding, the probe system being operated in a B-mode providing conical imaging.

In one embodiment, the probe system further comprises at least one of a Doppler OCT unit for performing Doppler measurements and a speckle variance OCT unit.

According to another broad aspect of the present invention, there is provided a spectral absorption and low coherence interferometry probe system for evaluating proximity to a tissue layer, comprising a light source for generating excitation light having at least one wavelength adapted for absorption by blood chromophores and low coherence, an excitation optical fiber to bring the excitation light near the tissue layer and a collection optical fiber for capturing back-scattered light from the tissue layer. The probe system comprises a light detector operatively connected to the collection optical fiber and a digital signal processor operatively connected to the light detector for determining a distance to the tissue layer based on the back-scattered light and on Beer-Lambert law of light absorption using a value for surrounding tissue attenuation coefficient ($\mu$eff). The probe system comprises a low coherence interferometry sub-system operatively connected to the excitation optical fiber and the collection optical fiber and having a beam splitter and a reference mirror. The probe system also comprises a signal processor operatively connected to the low coherence interferometry sub-system for evaluating a distance to the tissue layer based on the back-scattered light received by the collection optical fiber.

In one embodiment, the excitation optical fiber comprises a single mode fiber and the collection optical fiber comprises a single mode fiber for OCT mode light collection and a multimode fiber for spectral absorption mode light collection.

In a further embodiment, the probe system comprises a forward-looking transverse scanner enabling B-mode imaging.

According to another broad aspect of the present invention, there is provided a spectral absorption probe method for evaluating proximity to an artery, comprising: generating an excitation light having a wavelength adapted for absorption by blood chromophores; bringing the excitation light near the artery; capturing back-scattered light from the artery; and processing the back-scattered light from the artery for determining a distance to the artery based on Beer-Lambert law of light absorption using a value for surrounding tissue attenuation coefficient ($\mu$eff).

In one embodiment, the method is used for evaluating proximity to an inferior alveolar nerve in situ.

In one embodiment, the method further comprises monitoring oxygen saturation levels to maintain an inline calibration of arterial blood absorption properties.

In one embodiment, the method further comprises determining the surrounding tissue attenuation coefficient ($\mu$eff) according to absorption and scattering in surrounding tissue of a calibration excitation signal.

In one embodiment, the back-scattered light is captured angularly and at a given distance with respect to the brought excitation light.

In one embodiment, the method further comprises using a vascular contrast agent.

According to another broad aspect of the present invention, there is provided a low coherence interferometry probe method for evaluating proximity to a tissue layer, comprising: generating a low coherence excitation light; bringing the low coherence excitation light near the tissue layer; capturing back-scattered light from the tissue layer; performing interferometry between the low coherence excitation light and the back-scattered light for providing an interference signal; and processing the interference signal for evaluating a distance to the tissue layer.

In one embodiment, the method is used for evaluating proximity to an inferior alveolar nerve in situ.

In one embodiment, the probe method is operated according to A-mode.

In another embodiment, the method further comprises forward-looking transverse scanning of the tissue layer for enabling B-mode imaging.

In one embodiment, the method further comprises using an optical clearing agent at a probing site.

According to another broad aspect of the present invention, there is provided a spectral absorption and low coherence interferometry probe method for evaluating proximity to a tissue layer, comprising: generating an excitation light having at least one wavelength adapted for absorption by blood chromophores and low coherence; bringing the excitation light near the tissue layer; capturing back-scattered light from the tissue layer; processing the back-scattered light for determining a first distance to the tissue layer based on Beer-Lambert law of light absorption using a value for surrounding tissue attenuation coefficient (µeff); performing interferometry between the low coherence excitation light and the back-scattered light for providing an interference signal; and processing the interference signal for evaluating a second distance to the tissue layer.

BRIEF DESCRIPTION OF THE DRAWINGS

Having thus generally described the nature of the invention, reference will now be made to the accompanying drawings, showing by way of illustration a preferred embodiment thereof and in which.

It will be noted that throughout the appended drawings, like features are identified by like reference numerals.

DETAILED DESCRIPTION

Anatomy Background

Figure 1:
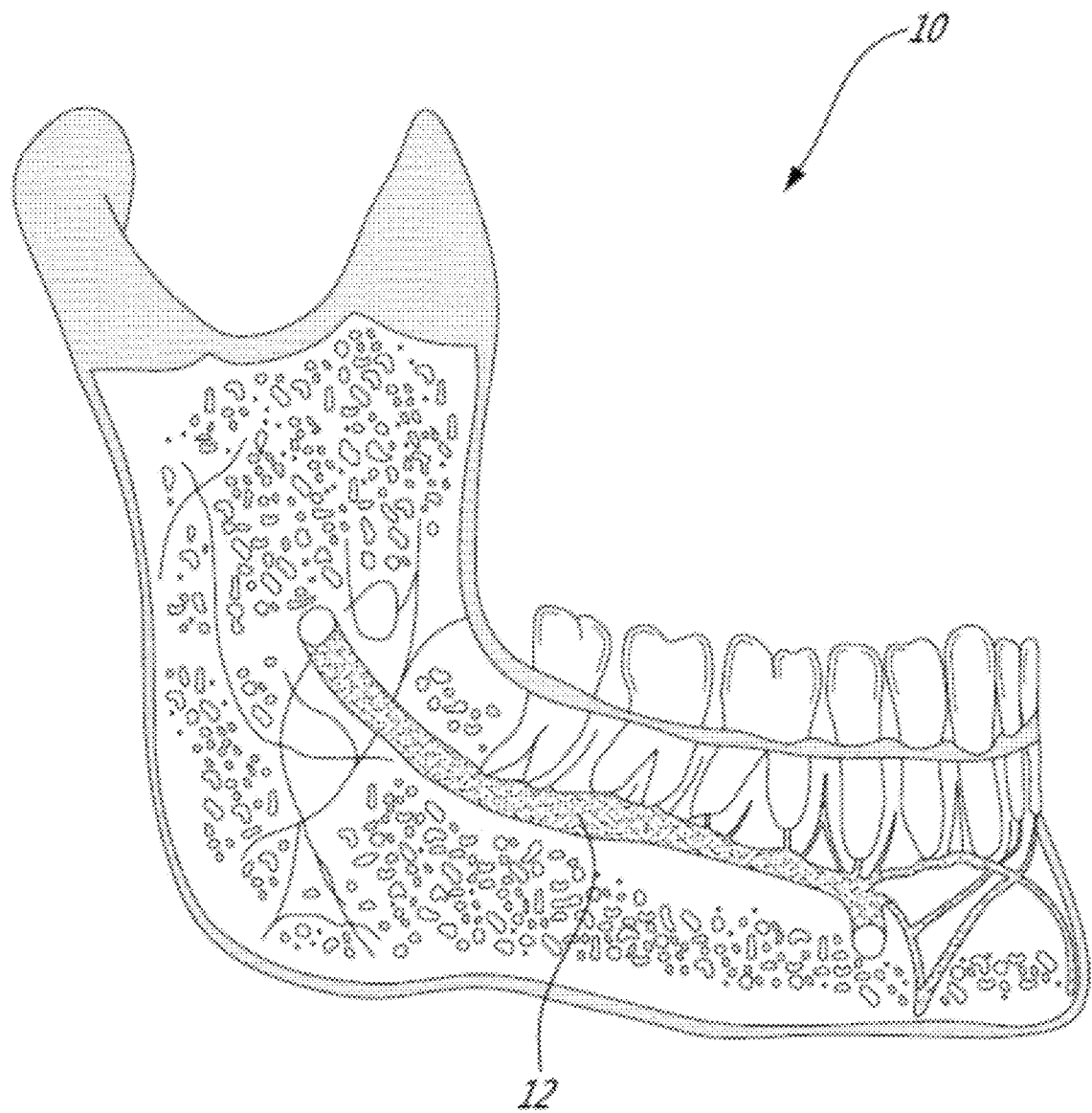
FIG. 1 is a sagittal section of a mandible showing the inferior alveolar nerve (IAN) positioned directly underneath the molar teeth.
Figure 2:
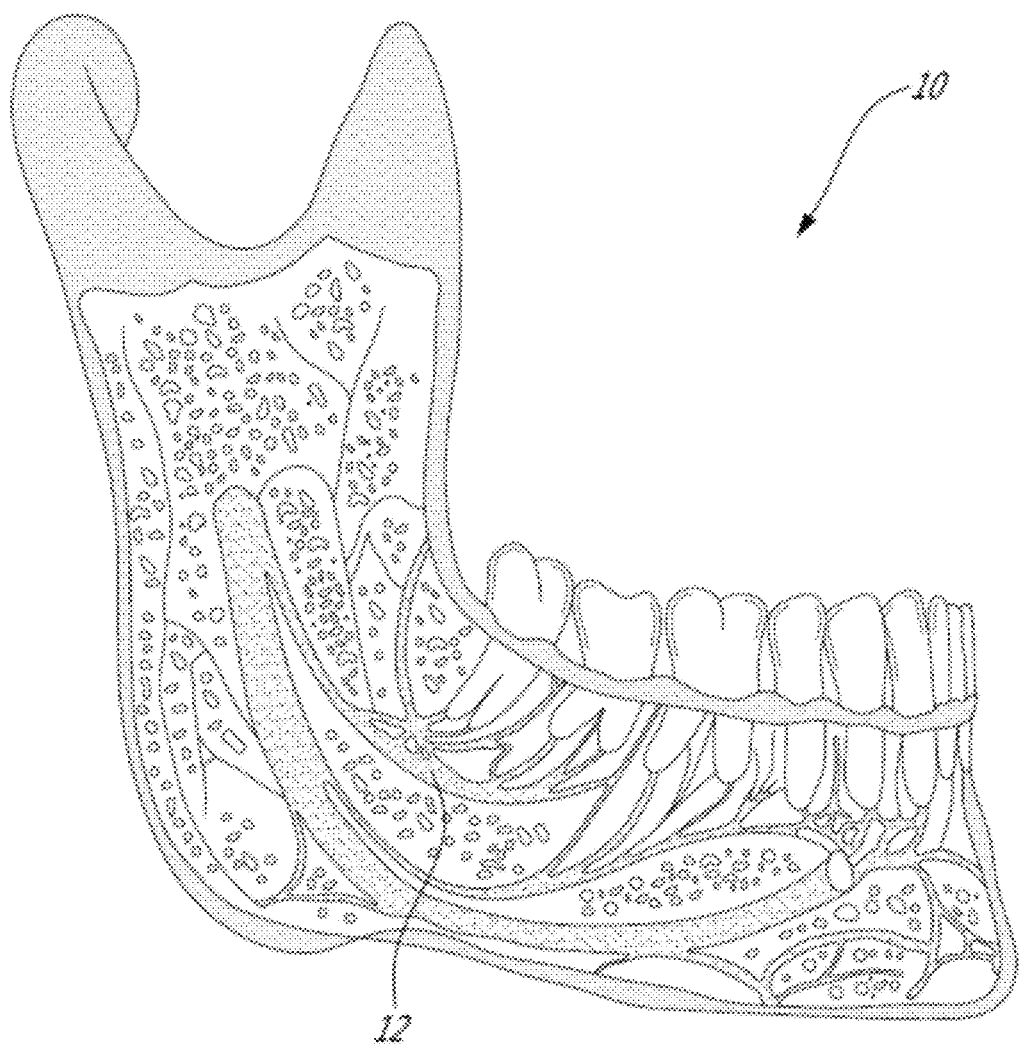
FIG. 2 is a sagittal section of the inferior alveolar nerve (IAN) positioned at the bottom of the mandible.

Referring to FIGS. 1 and 2 which show Sagittal sections of a mandible 10, the inferior alveolar nerve 12 (IAN) is a branch of the mandibular nerve, which stems from the trigeminal nerve system. The IAN 12 enters an intraosseous canal through the mandibular foramen in the posterior portion of the mandible. The nerve continues its path within the mandible 10 and then exits through the mental foramen. Throughout the length of the osseous canal, the IAN 12 is closely associated with the inferior alveolar artery and both structures are covered in a tough sheath of connective tissue. The diameter of the entire bundle varies between patients but averages at 2.53±0.29 mm [C. D. Morris et al., *J. Oral Maxillo. Surg.*, 68:2833-2836, 2010].

The intraosseous canal is a hollow channel and in most cases has borders with defined walls which may be consistent throughout the length of the canal. The diameter of this canal is known to be 2.0 to 2.6 mm. The canal walls may either be composed of cortical bone, or in lesser frequency, may be continuous and uniform with the surrounding trabecular bone. Many patients have canals which abruptly become uniform and continuous with surrounding cancellous bone within proximity of the mental foramen. Although the intraosseous canal is present in many patients, it is not a consistent feature within the mandibles of every individual. Dissection studies show that cortical walls and distinct osseous canals within mandibles are not always present. Some specimens of IAN were shown to travel the trabecular marrow spaces without any defined canal present.

The position of the IAN 12 within the mandible 10 is highly variable. In one dissection study, the position of the IAN varied in position from the sub-dental portion below the molar roots (See FIG. 1), to an inferior position near the bottom ridge of the mandible 10 (See FIG. 2). A feature which was not frequent, but was observed, was the splitting of the IAN bundle into diffuse branches without a defined intraosseous canal.

Current IAN Location Methods

The general imaging methods currently used by surgeons to assess the position of the IAN are Panoramic X-ray, Computed Tomography (CT) scan, and Microradiograph (MR) imaging. As some patients may lack an osseous canal and an IAN bundle altogether, pre-operative imaging is imperative. X-rays are usually taken in a panoramic fashion, encircling the entire mandible. This presents a global view of the mandible and images potential implant placement sites. The limitations of this technique are that it provides no information about mandible thickness and suffers from a distortion factor of about 25%. A more modern approach to the imaging of the mandible is the CT scan. This method is able to generate over-lapping images through computer software programs. However, for dental surgical purposes, only bone and calcified structures are imaged by CT; the IAN and associated non-osseous tissues are not. Thus the CT scan is limited for patients without defined canal walls; locating the IAN on a single cross section is difficult. Reformatted images of adjacent parallel and perpendicular images must be taken and used to assess the exact relative location of the IAN within the mandible. Detailed X-ray imaging, or Mircoradiograph (MR) imaging, is able to image and provide a notable contrast between osseous and non-osseous tissues. When using MR, the canal is visible in cross-sectional reformations exclusive of the osseous tissue surrounding it. The drawback to using MR imaging is that spatial distortions on MR images may not give proper resolution for smaller distances. This is also true for both CT and Panoramic scans, although the resolution for both these techniques has been shown to be similar. Current CT based technologies are expanding imaging possibilities by integrating novel software and 3-D imaging methods.

The drawback for all these imaging methods, with the exception of novel 3-D CT scanning methods, is that they are not in real time and must be performed preoperatively before the surgical procedure. These methods are also limited in resolution (typ. ±1.3 mm) and may not be able to properly image diffuse IAN layouts for patients without a localized IAN bundle. This adds much uncertainty and leaves the surgeon to estimate the exact locations of the IAN during surgery. Thus, a technology which combines both the procedures of drilling and localization of the IAN into a simultaneous process has yet to be developed.

Machining of Bone and Present Drill Sensor Technology

In the process of dental implants, drilling is used to create channels within the mandible for the placement of artificial roots.

The drilling operation performed on the mandible must traverse a cortical bone layer and into a cancellous bone mass. As the drill continues forward, heat is generated at the apex of the drill bit. Some of this heat is absorbed by the surrounding bone, raising its temperature. An implication of temperature rise and heat generation from machining bone is thermal osteonecrosis. Irreversible thermal osteonecrosis occurs when bone temperature reaches and exceeds 47° C. With irreversible osteonecrosis, adequate osseointegration could be inhibited, thus reducing the chances for a successful implant. When drilling bone without external irrigation, tissue temperatures can range from 31-56° C. An irrigation system is included in most surgical drills for this purpose. Water is injected through an orifice from the apex of the drill bit into the immediate drilling site. This acts to cool the drilling site, and functions to prevent thermal osteonecrosis. For the contribution of heat generation from the drill itself, the most important parameters are drill speed, feed rate and drill diameter. Hence with irrigation, adjustment and control of these parameters can help to reduce heat generation when drilling in bone.

Currently, drill sensor technology is not aimed at discerning the media situated at the drill-bone interface. Technology is more focused on detecting and imaging wear on drill burs and machinery. There exists drill detection systems aimed at bone machining applications. A mechatronic system developed by Bouazza-Marouf and Ong [Ong, F. R., Bouazza-Marouf, K.; 1999; The detection of drill bit break-through for the enhancement of safety in mechatronic assisted orthopaedic drilling; MECHATRONICS 9: 565-588] is able to discern drill break-through from inherent fluctuations in bone structure when drilling long bones. This system is able to detect differences in force through an electronic logic algorithm. The drawback here is that a certain, constant force is applied and the drill bit feed rate into the bone media is constant. In practice, drilling with constant force and feed rate would not be used due to variability in bony tissues within the body and between patients. The mechatronic system was also not able to discern latent non-osseous tissue. The application of this system for the purpose of long implant placement within the mandible would not be desirable as bone breakthrough is the arresting factor for this system.

Optical-Based In Situ Proximity IAN Sensor

Current surgery practice allows for an experienced dental surgeon to drill the mandible down to a distance of 2 mm from the IAN, without too much risk of damaging the nerve bundle. As such, the proximity sensor operating range should be within this 2 mm boundary, although a longer distance of operation would be useful. At the same time, the axial resolution of the sensor should be as high as possible.

The first approach is based on Low Coherence Interferometry (LCI). A LCI probe can be built to operate in A-mode (i.e. point-scan only, no image). LCI presents similar results to ultrasound echolocation and provides a high-resolution measurement of the tissue layers structure based on back-scattered light intensity from those layers. The measurements being optical in nature, the axial resolution of this technique is at least ten times better than with ultrasound, at the cost of a much lower depth penetration (typ. resolutions in ~10 µm at maximal depths of ~1.5 mm, depending on tissues optical absorption and scattering properties). The particular imaging extension of this technique, i.e B-mode scanning, is known in the art as Optical Coherence Tomography (OCT).

Figure 3:
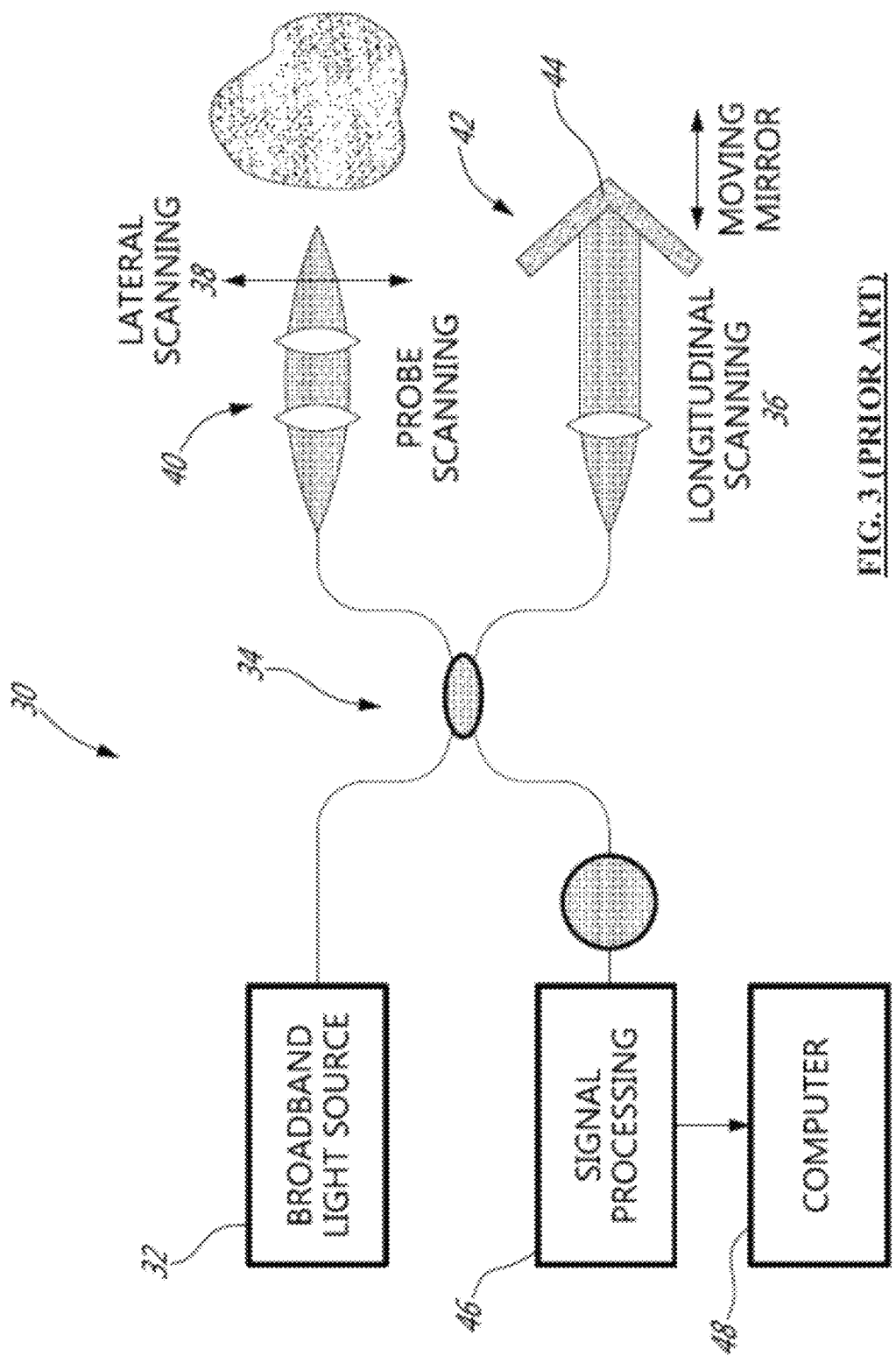
FIG. 3 (Prior Art) is a diagram of a standard time-domain Optical Coherence Tomography setup of the prior art.
Figure 4B:
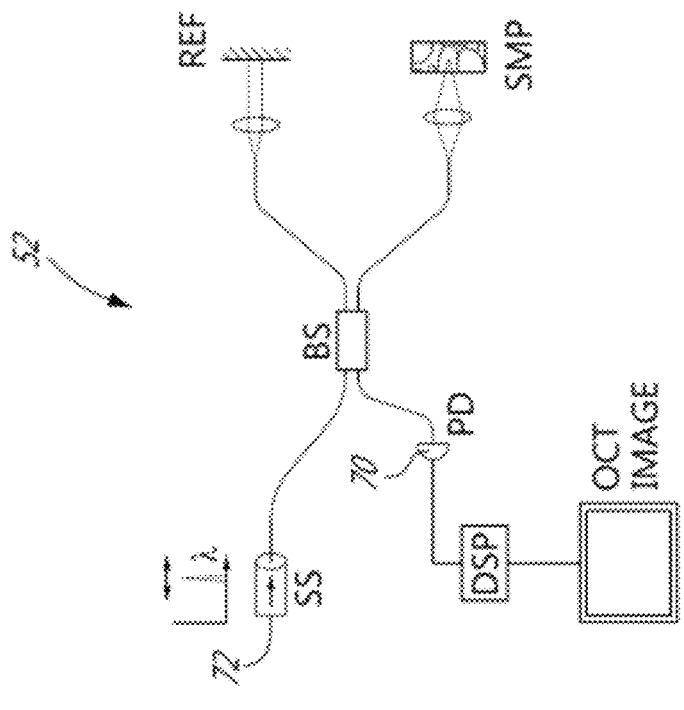
FIG. 4B (Prior Art) is a diagram of a frequency-swept-source-based OCT system, or time-encoded Fourier-Domain OCT system (TEFD-OCT)
Figure 4A:
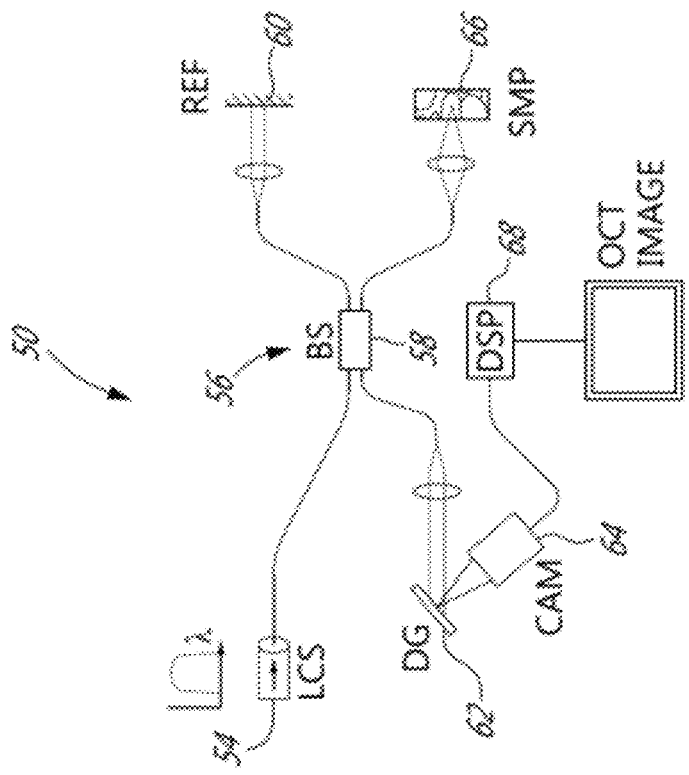
FIG. 4A (Prior Art) is a diagram of a spatially-encoded Fourier-domain OCT system (SEFD-OCT)

FIG. 3 shows an embodiment of a standard time-domain LCI or OCT system 30 using a low coherence light source 32 (typically a superluminescent LED or pulsed laser) and an interferometer configuration 34 for performing a longitudinal scanning 36 and a lateral scanning 38. As illustrated, an optical arrangement 40 is used for implementing the lateral scanning 38 while an optical arrangement 42 comprising a moving mirror 44 is used for implementing the longitudinal scanning 36. A signal processor 46 may be used in conjunction with a computer 48 for signal processing purposes. Newer designs, as the systems 50 and 52 shown in FIGS. 4A and 4B respectively, involve detecting in the Fourier domain or using frequency-swept light sources to disband with the traditional time-pulsed requirement of the incident light emission. The system 50 comprises a low coherence source (LCS) 54, an interferometer sub-assembly 56 provided with a beamsplitter (BS) 58 and a reference mirror (REF) 60. The system 50 also comprises a diffraction grating (DG) 62 and a camera (CAM) 64 for detecting light back-scattered by the sample (SMP) 66. A digital signal processor (DSP) 68 is operatively connected to the camera 64 for providing an OCT image based on the back-scattered light. The system 52 of FIG. 4B uses a swept source (SS) 72 in place of the low coherence source 54 of FIG. 4A and a photodetector (PD) 70.

An A-Mode fibered LCI probe can be designed in a compact form small enough to fit within a dental drill bit, according to one embodiment. Tissue interfaces will appear as an increase in the back-scattered signal intensity. Similarly, in an alternative embodiment, a B-mode 2D image can be generated by building the LCI/OCT probe with an integrated forward-looking proximal or distal scanner, as it should become apparent to the skilled addressee. In the case of the IAN, an interface signal will be generated either by the canal wall or the nerve bundle itself and will be visible in real time to the dental surgeon as long as the interface is within the penetration depth range of the instrument.

Figure 5:
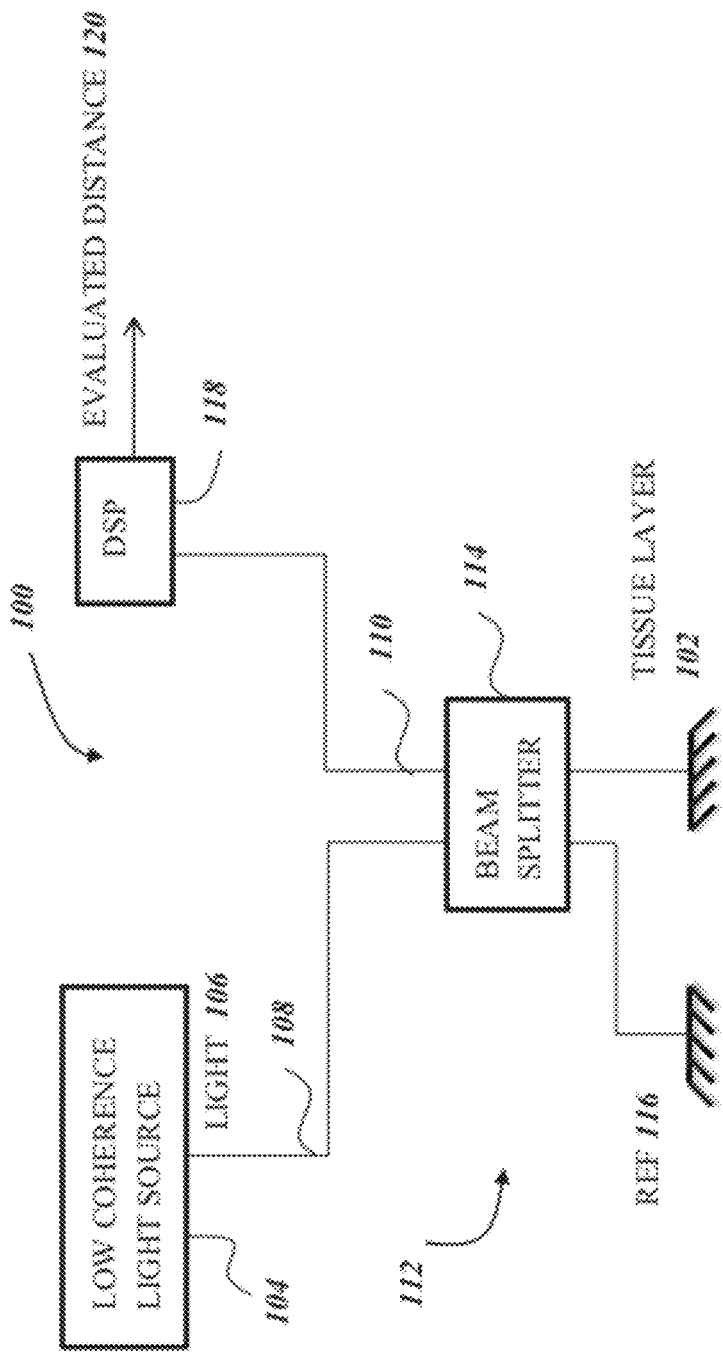
FIG. 5 is a schematics of a low coherence interferometry probe system for evaluating proximity to a tissue layer, according to one embodiment.

FIG. 5 illustrates a low coherence interferometry probe system 100 for evaluating proximity to a tissue layer 102, according to the above detailed technique and according to one embodiment. The probe system 100 comprises a low coherence light source 104 for generating low coherence excitation light 106, an excitation optical fiber 108 to bring the low coherence excitation light 106 near the tissue layer 102 and a collection optical fiber 110 for capturing backscattered light from the tissue layer 102. The probe system 100 also comprises a low coherence interferometry sub-system 112 operatively connected to the excitation optical fiber 108 and the collection optical fiber 110 and having a beam splitter 114 and a reference mirror 116. A digital signal processor 118 operatively connected to the low coherence interferometry sub-system 112 is used for evaluating a distance 120 to the tissue layer 102 based on the back-scattered light received by the collection optical fiber 110.

Figure 17:
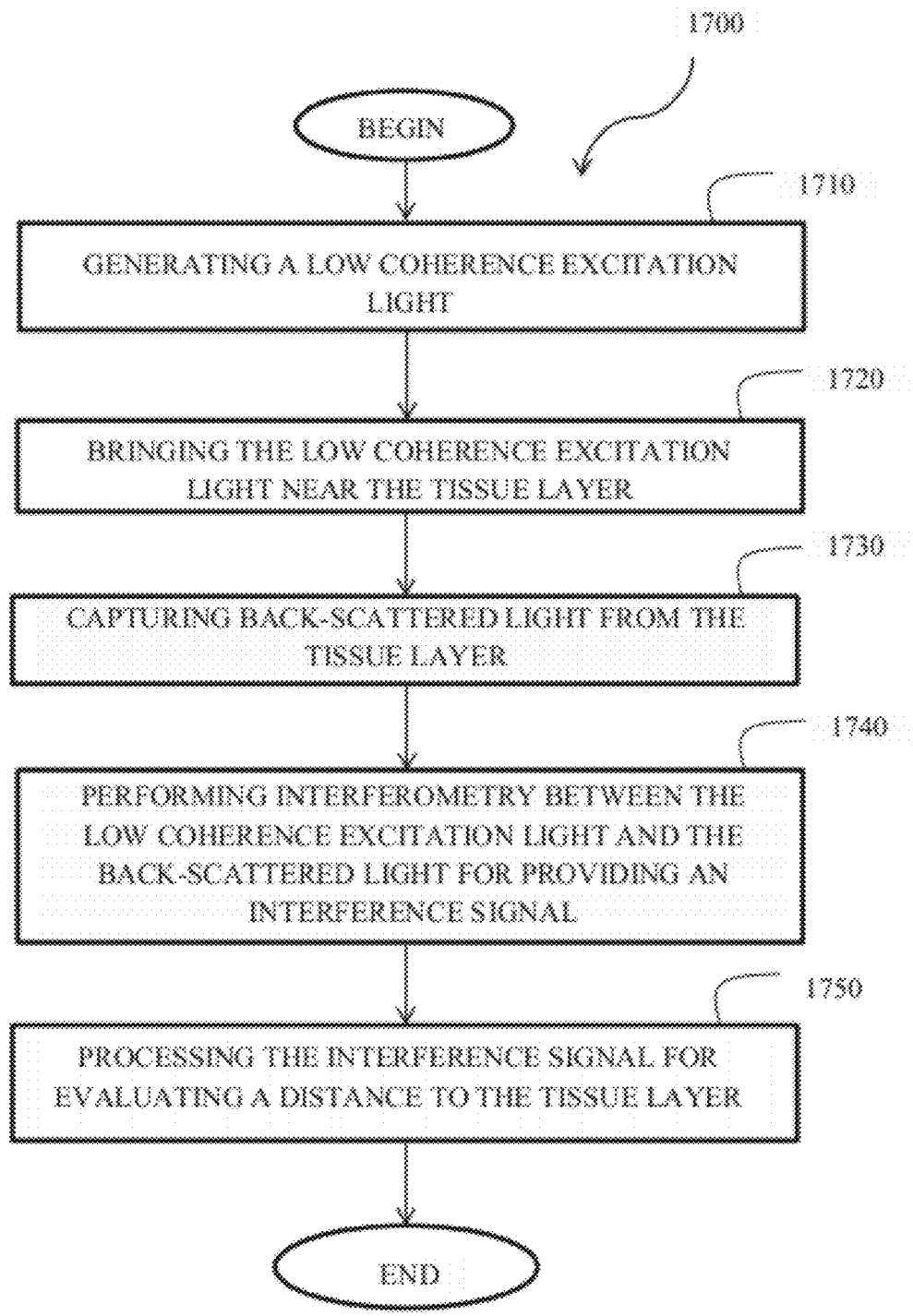
FIG. 17 is a flow chart of a probe method for evaluating proximity to a tissue layer, according to one embodiment.

FIG. 17 illustrates a low coherence interferometry probe method for evaluating proximity to a tissue layer, according to one embodiment. According to processing step 1710, a low coherence excitation light is generated. According to processing step 1720, the low coherence excitation light is brought near the tissue layer. According to step 1730, back-scattered light from the tissue layer is captured. According to processing step 1740, interferometry between the low coherence excitation light and the back-scattered light is performed for providing an interference signal. According to processing step 1750, the interference signal is processed for evaluating a distance to the tissue layer.

Experiments were conducted with a probe system 100 on a post-mortem extracted human jawbone cut in such a way that the LCI entry point surface made a wedge with the approximate location of the canal, thus providing increased depth of the IAN interface with the entry point location. This approach allows to evaluate the depth penetration of the technique. The results indicate a probing range of about 1 mm within the test conditions (ex vivo sample, wavelength of 1.32 µm). An increase in wavelength should improve detection range as tissue scattering decrease monotonically with wavelength. However, one must also fine tune the wavelength so that it fits between tissue absorption lines that are numerous in these ranges due to tissue water content. Appropriate designs for performing LCI/OCT systems seem to favor the use of frequency-swept laser sources for state-of-the-art devices. Availability of such light sources at 1.55 µm is increasing and development at 1.8 µm is ongoing. The skilled addressee will nevertheless appreciate that other arrangements may be considered.

A second optical approach is to use the spectral absorption properties of arterial blood and the blood flow dynamics (change in blood volume due to the patient's pulse) to measure the distance to this artery based on the Beer-Lambert law of light absorption:

$$I = I_0 \exp(-\mu_{eff} d) \quad [1]$$

where $I$ and $I_0$ are the detected and incident light intensities, respectively, d is the total propagation distance of the light within tissues (the sensor will measure the distance s=d/2) and $\mu_{eff}$ is the attenuation coefficient of the medium in which light propagation occurs. In the case of tissues, attenuation is a combination of absorption and scattering of the photons at the illumination wavelength and is tissue-type-dependent.

Figure 16:
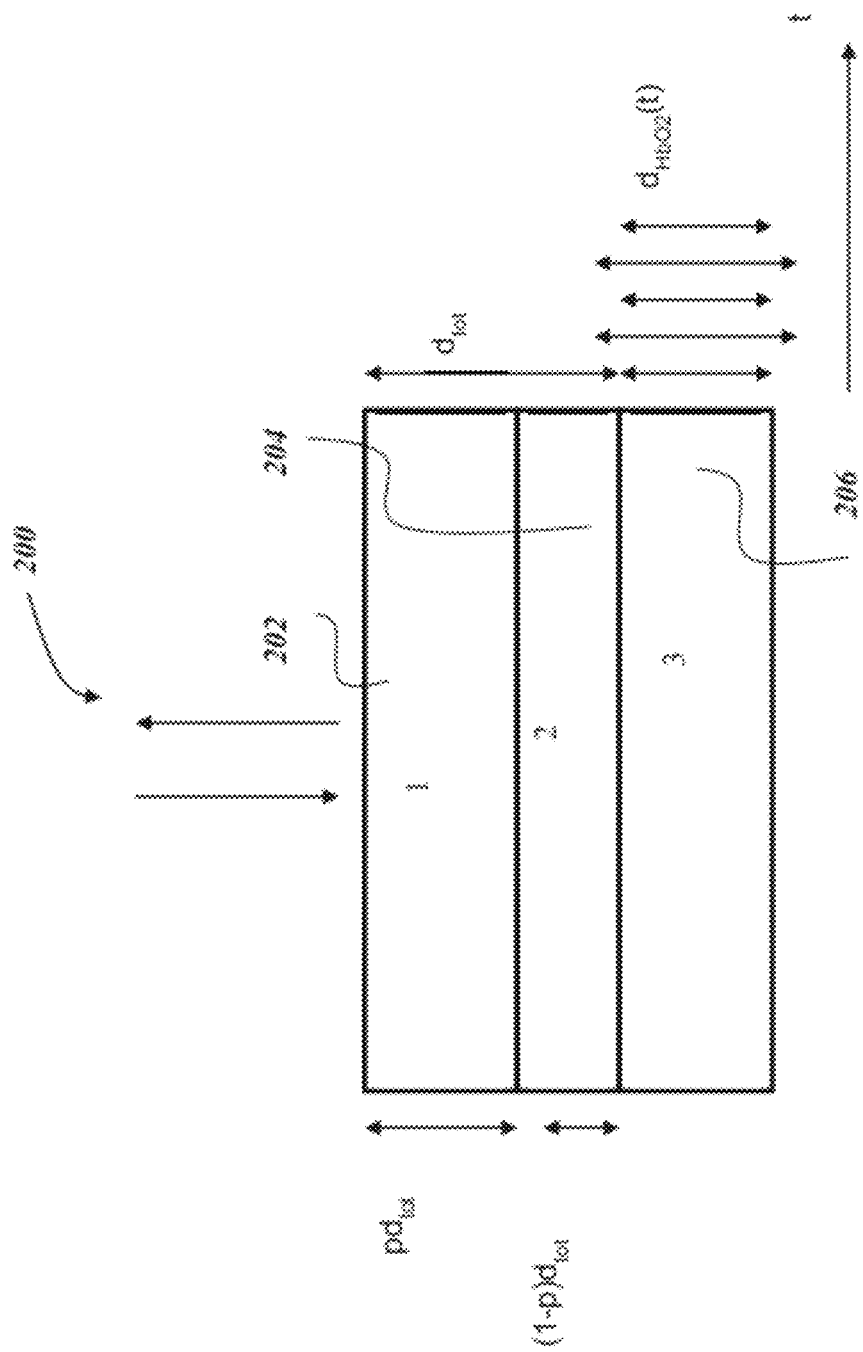
FIG. 16 is a diagram of a one dimensional model of a trabecular bone, according to one embodiment.

A first approximation model can provide an evaluation of the order of magnitude of the return signal. The probing device would operate from within the trabecular bone to identify the artery from the IAN neurovascular bundle. Trabecular bone is a complex structure composed of cortical bone and bone marrow arranged in "cells", similar to a beehive. Optically, this structure may be represented in a one dimensional model 200 where three layers 202, 204, 206 are stacked vertically, each representing cortical bone, bone marrow and arterial blood, as illustrated in FIG. 16. In this model, the blood layer thickness varies over time in a periodic fashion to represent the blood volume change in the arteries due to the cardiac cycle. The thickness of the bone and marrow layers is dependent on the porosity of the trabecular structure.

Using this representation, the equations governing the optical propagation, based on the Beer-Lambert's Law, are:

$$I = I_0 e^{-[\mu_{marrow} d_{marrow} + \mu_{cortical} d_{cortical} + \mu_{HbO2}(t) d_{HbO2}(t)]} \quad (2),$$

where $\mu_x$ and $d_x$ (x=marrow, cortical, HbO2) are the attenuation coefficient and layer thickness of each of the three types of tissue involved. The marrow and cortical layer thicknesses are related to the porosity of the trabecular structure 0<p<1 such that:

$$d_{marrow} = p \times d_{total}$$

$$d_{cortical} = (1-p) \times d_{total} \quad (3),$$

where $d_{total} = d_{marrow} + d_{cortical}$ is the total thickness of trabecular bone between the light input and the arterial layer. Because of blood flow and its properties, the HbO2 terms are time-dependent. Indeed, the distance parameter $d_{HbO2}$ will change due to the volume variation occurring with pulsating blood flow. In the proposed model 200, this is represented by a harmonic variation of the thickness of the arterial layer:

$$d_{HbO2}(t) = d_{HbO2-baseline}(1 \pm \Delta_d \cos(2\pi f t)) \quad (4),$$

where $d_{HbO2-baseline}$ is the average thickness of the layer, $0 < \Delta_d < 1$ is the maximum fractional thickness change due to pulsating blood flow, t is time and f is the blood pulse frequency in Hz.

The HbO2 attenuation coefficient should also be considered a time-dependent value as it is related to blood oxygenation levels in the patient, thus dependent on the proportions of oxy- and deoxy-hemoglobin in arterial blood. In practice, however, the variation of blood oxygenation will generally be on a much longer time scale than the variations due to the patient's pulse. Strong and sudden variations of blood oxygenation are rare and indicative of a serious health condition that is unlikely to be encountered in the normal operation of the IAN sensor. Nevertheless, monitoring of blood oxygenation with a pulse oximeter is considered a good practice in the utilization of such a sensor, if only as a check point for the sensor's calibration, as detailed below. For the sake of the proposed model, the attenuation coefficient was however assumed to be a constant.

Combining Eqs. (2)-(4), the model was built to provide an order of magnitude for the optical signal intensity over time to be expected from such an approach. The resulting output optical power is described with:

$$I(t) = I_0 \exp[-\{p(\mu_{marrow} - \mu_{cortical}) + \mu_{cortical}\} d_{total} - \mu_{HbO2} d_{HbO2-baseline}(1 \pm \Delta_d \cos(2\pi f t)] \quad (5).$$

The near infrared spectroscopy (NIRS) based sensor goal is to measure the thickness $d_{total}$ of trabecular bone tissue between the probe (or drill) tip and the neurovascular bundle containing the IAN. In one embodiment, a lock-in amplifier may be used to establish the magnitude of the oscillating signal and circumvent the DC signal that is influenced by the static trabecular tissue, as detailed below. In one embodiment, a typical method is to use the root-mean square value of the AC signal:

$$I_{RMS} = \sqrt{\langle I^2(t) \rangle} \quad (6),$$

where:

$$\langle I^2(t) \rangle = \int_0^{1/f} t[I(t)]^2 dt. \quad (7)$$

Solving Equ. (6) from (5) and (7) and using a Taylor expansion for the exponential function up to the second degree in the integral leads to:

$$I_{RMS} \approx \left[\sqrt{2}\, I_0 \frac{1}{2f}\sqrt{1+B^2\Delta_d^2}\right] e^{-Kd_{total}+B}; \quad (8)$$

$$B = \mu_{HbO2} d_{HbO2-baseline};$$

$$K = p(\mu_{marrow} - \mu_{cortical}) + \mu_{cortical},$$

and thus, $$d_{total} \approx \left\{ \mu_{HbO2} d_{HbO2-baseline} - \ln\left(\sqrt{2}\, f\left(\frac{I_{RMS}}{I_0}\right)\frac{1}{\sqrt{1+(\Delta_d \mu_{HbO2} d_{HbO2-baseline})^2}}\right)\right\} \frac{1}{p(\mu_{marrow}-\mu_{cortical})+\mu_{cortical}}. \quad (9)$$

With such a model, assuming an input of 10 mW of optical power at the proper wavelength, an output signal of approximately 0.07 mW would be produced.

Figure 7:
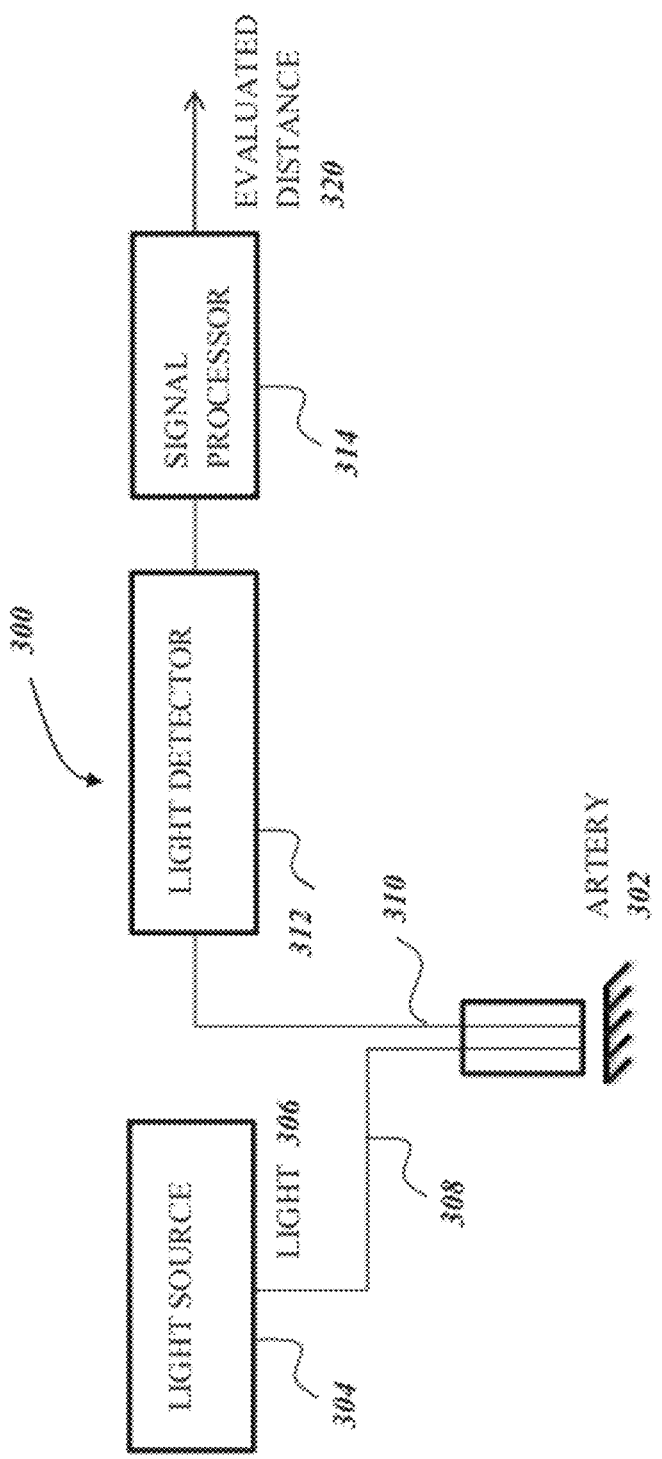
FIG. 7 is a schematics of a spectral absorption probe system for evaluating proximity to an artery, according to one embodiment.

FIG. 7 shows a spectral absorption probe system 300 for evaluating proximity to an artery 302, according to the above detailed technique and according to one embodiment. The probe system 300 comprises a light source 304 for generating excitation light 306 having a wavelength adapted for absorption by blood chromophores, an excitation optical fiber 308 to bring the excitation light 306 near the artery 302 and a collection optical fiber 310 for capturing back-scattered light from the artery 302. The probe system 300 comprises a light detector 312 operatively connected to the collection optical fiber 310 and a signal processor 314 operatively connected to the light detector 312 for determining a distance 320 to the artery 302 based on the back-scattered light and on Beer-Lambert law of light absorption using a value for surrounding tissue attenuation coefficient (µeff).

Figure 18:
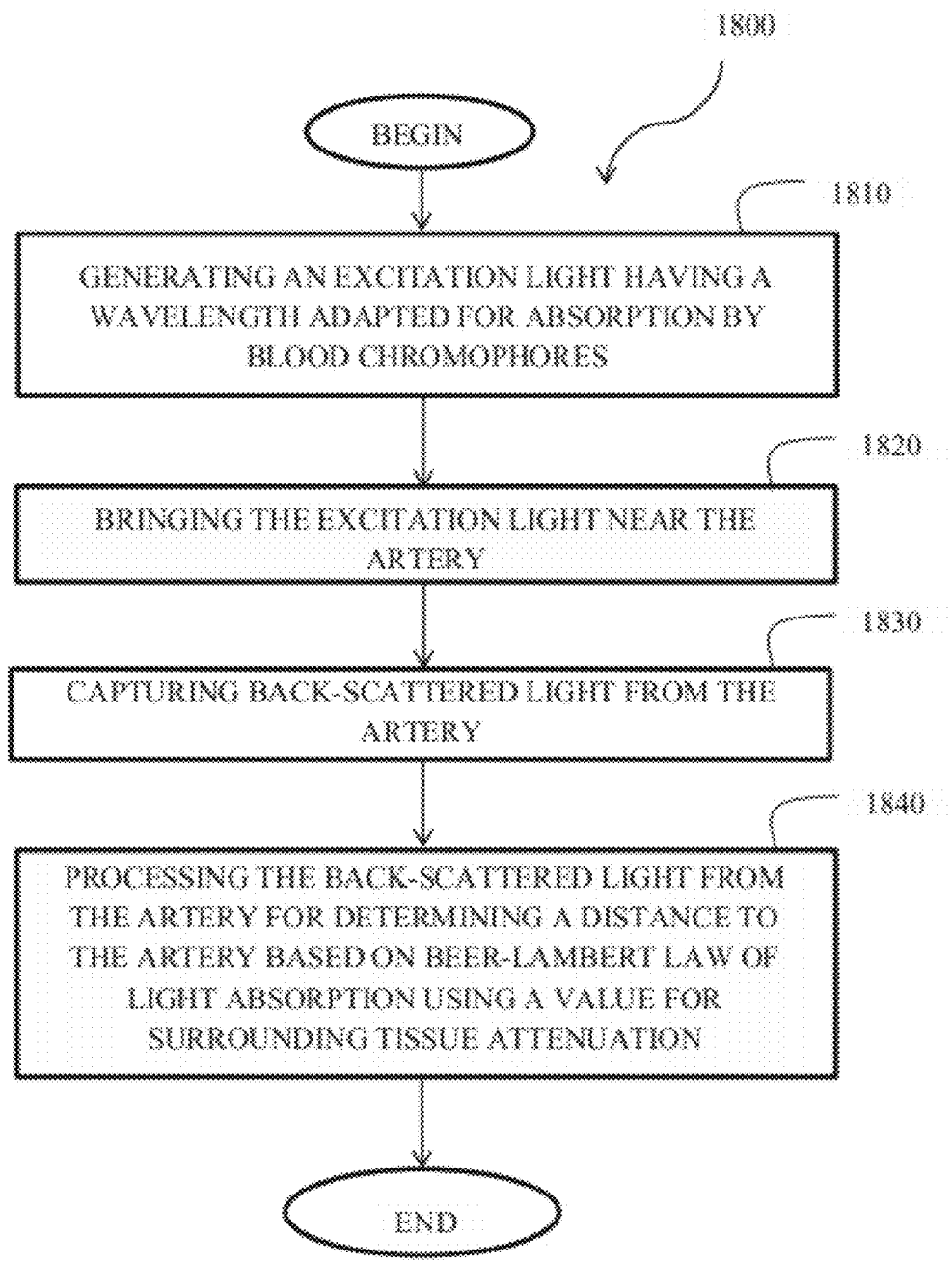
FIG. 18 is a flow chart of a probe method for evaluating proximity to an artery, according to one embodiment.

FIG. 18 illustrates a spectral absorption probe method for evaluating proximity to an artery, according to one embodiment. According to processing step 1810, an excitation light having a wavelength adapted for absorption by blood chromophores is generated. According to processing step 1820, the excitation light is brought near the artery. According to processing step 1830, back-scattered light is captured from the artery. According to processing step 1840, the back-scattered light from the artery is processed for determining a distance to the artery based on Beer-Lambert law of light absorption using a value for surrounding tissue attenuation coefficient (µeff).

Figure 6:
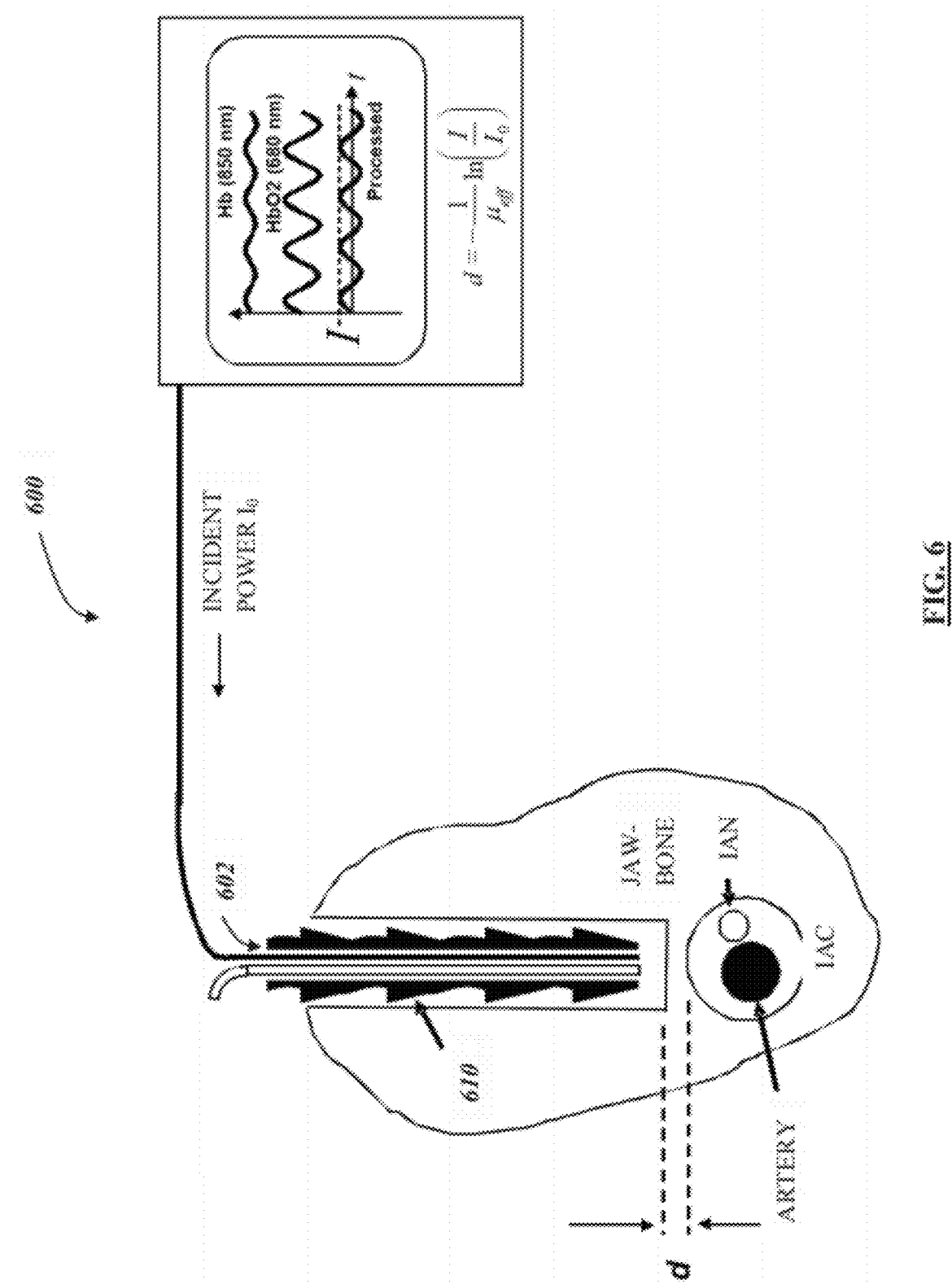
FIG. 6 is a concept schematics of a drill-integrated IAN sensor based on the NIR spectral absorption technique, according to one embodiment.

As anatomically the artery is part of the IAN bundle, locating it is almost equivalent to locating the nerve. This approach can be implemented in a similar package as the LCI/OCT fiber probe that can fit within the dental drill bit. The blood pulse can be used to eliminate all background signals via AC-coupling of the detector or lock-in amplification. The signal amplitude can then be used to assess the distance from the probe to the IAN bundle based on Beer-Lambert's law. A calibration process is however typically required before use in situ due to patient's tissues variability of optical properties. Notably, the approach relies on the absorption of oxyhemoglobin, which itself will potentially vary according to blood oxygen saturation. As such, the approach might benefit from the probe being used in conjunction with a pulse oxymeter that would monitor oxygen saturation levels and thus, indirectly account for variations of the blood attenuation coefficient. A variation on this approach uses the same spectral principle as the pulse oxymeter, utilizing two wavelengths (typically, 660 nm to target deoxyhemoglobin and 850 nm to target oxyhemoglobin, but generally comprised between 650 nm and 900 nm), as shown in FIG. 6 which illustrates a drill-integrated IAN sensor 600 based on the NIR spectral absorption technique. As detailed therein, distance can be obtained by isolating the distance variable (d) in Equ. 1, but requires that the surrounding tissues' attenuation coefficient (µeff) be known through a calibration step. It has to be noted that such a technique would be limited in the precision of the measurement, as the signal output results from probing a large volume with diffused photons and is thus inherently averaging over that volume, which might skew the output value of distance. Using AC-coupling and a proper calibration is key in this approach, as detailed thereafter.

Figure 8:
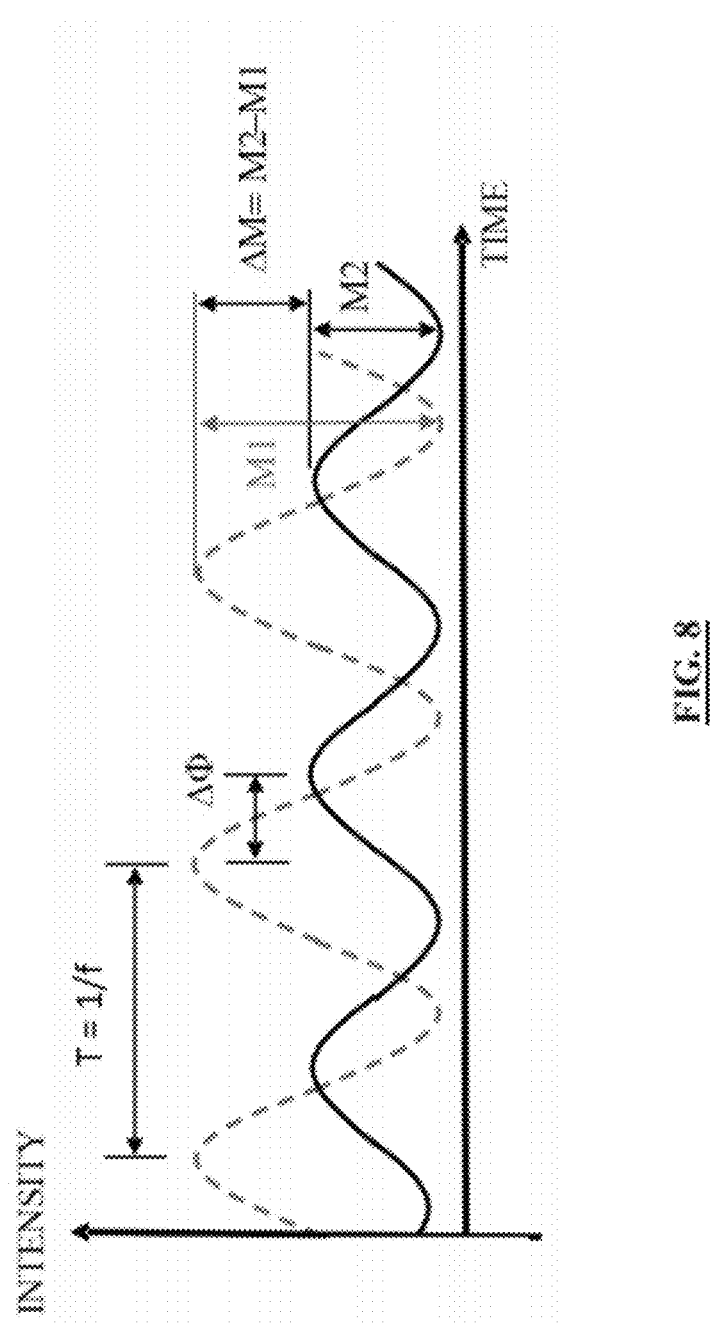
FIG. 8 is a graph illustrating impact of propagation in a turbid medium such as biological tissue on an intensity-modulated light beam.

In one embodiment, the calibration for the spectral absorption technique may be integrated within the standard configuration if a lock-in amplifier (not shown) is used. In such an embodiment, as illustrated in FIG. 8, an intensity-modulated light excitation of modulation frequency f (typ. ~100 MHz range) and modulation depth M1 propagating in the tissues will suffer phase retardation and reduction of the modulation depth as a function of the attenuation properties of the traversed medium. The retrieved signal has the same frequency as the incident one, but due to absorption and scattering in the medium, it suffers a phase shift ΔΦ and an attenuation of the modulation depth M2 relative to the incident signal. The change in phase ΔΦ and modulation depth ΔM is correlated to the average attenuation coefficient and can be used to extract the parameter $\mu_{eff}$ in Equ. 1. This method is known in the art of Diffuse Optical Tomography. To achieve accurate results, though, the modulation frequency should be in the range of about 100 MHz to 500 MHz. Unfortunately, limitations in current lock-in amplifier electronics make most affordable conventional devices to operate up to the hundreds of kHz range.

Figure 9:
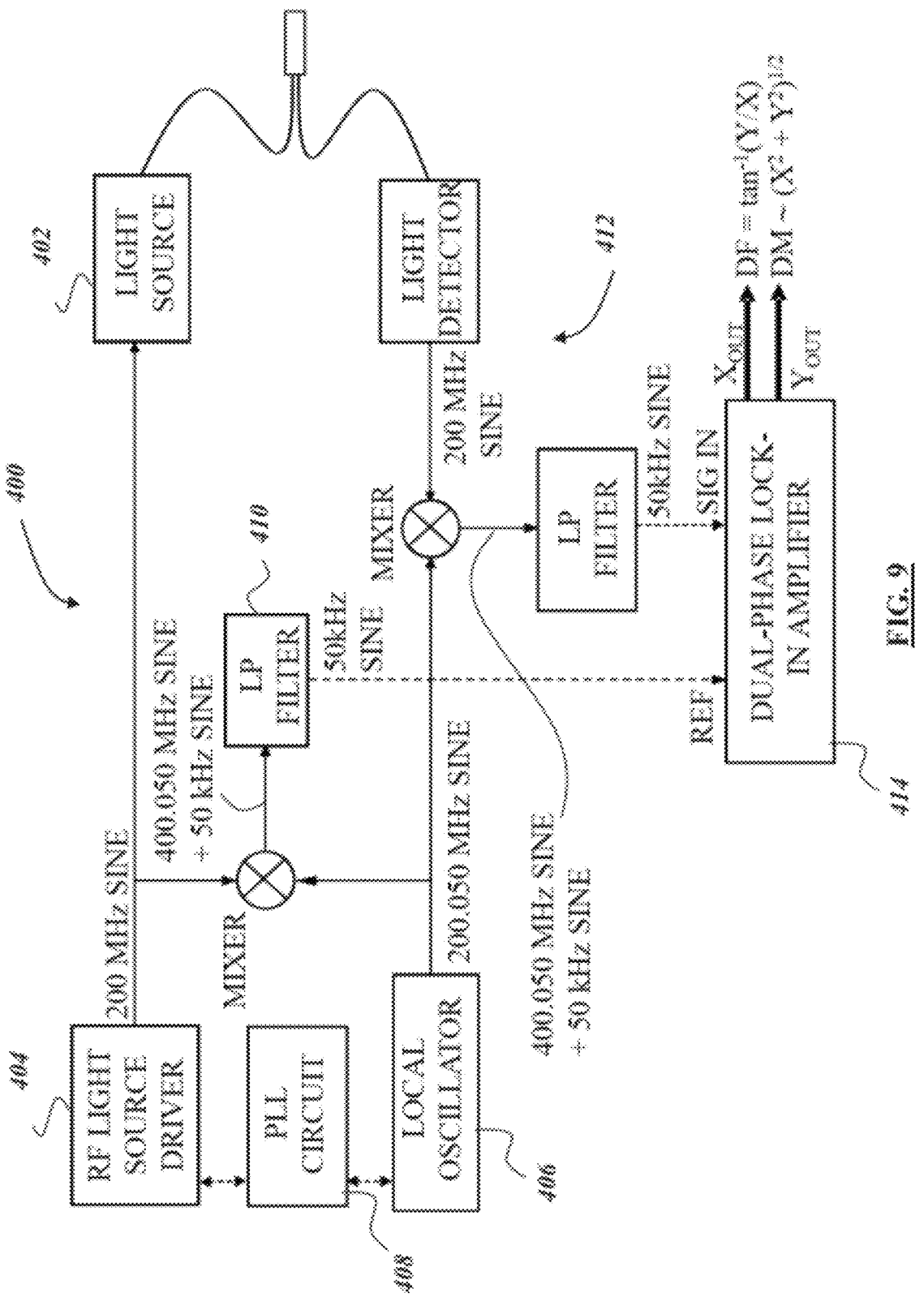
FIG. 9 is a schematics of a heterodyne detection configuration for a IAN sensor, according to one embodiment.

This issue can be solved by using a heterodyning processing circuit before the lock-in amplifier input, as illustrated in FIG. 9, using signal mixing with an intermediate frequency and using principles of Amplitude Modulation to extract the difference signal. In the illustrated embodiment of a probe system 400, the light source 402 is driven at high frequency with a light source driver 404, for example at 200 MHz, to insure adequate resolution on the extracted values ΔΦ and ΔM. A local oscillator 406 generates a slightly larger frequency, larger by 50 kHz as a non-limitative example. The oscillator 406 and the driver 404 are phase-locked by a PLL circuit 408. Mixing those two signals produces the sum and difference signals (amplitude modulation) and a low-pass filter 410 is used to retain only the difference component. The detection channel 412 operates similarly and a standard, low-bandwidth dual-phase lock-in amplifier 414 can then be used.

Furthermore, it is known in the art that the positioning of the probe for calibration (in contact or not with tissues and other variants) can skew the calibration measurement. The method might thus need an additional step where the instrument is pre-calibrated with an appropriate optical phantom (not shown) with known attenuation properties supplied with the device, before the in-patient calibration step. This way, a relative value to the phantom properties would be obtained and should be enough for the proper operation of the sensor.

With such an approach, the calibration of the device for the patient's jaw tissues may be made at the beginning or at an early phase of the drilling process by the surgeon, before enabling the sensor, which is of great advantage.

Embodiments and Possible Features of the Optical IAN Sensor

Figure 10:
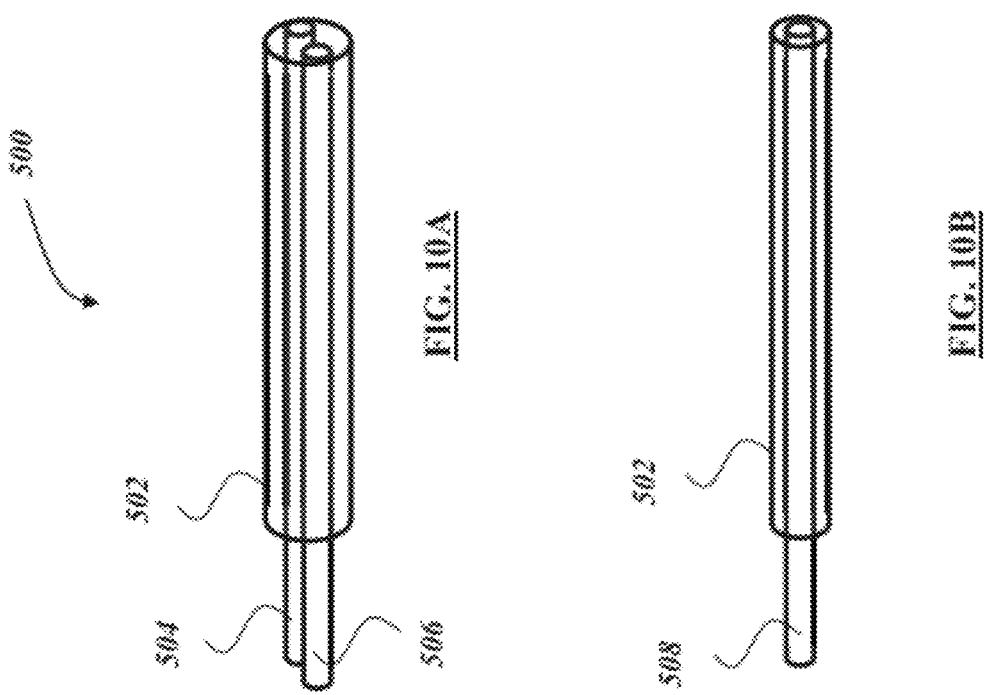
FIG. 10A is a schematics of an embodiment of a standalone IAN proximity sensor handpiece, according to a spectral absorption configuration.
FIG. 10B is a schematics of another embodiment of a standalone IAN proximity sensor handpiece, according to a OCT-based, single fiber configuration.

Different embodiments of the Optical IAN probe system can be envisioned for both approaches described above. The following is a short description of each of the potential embodiments and implementations envisioned:

Standalone Self-Contained Spectral Absorption-Based Fiber-Probe:

FIG. 10A shows an embodiment wherein the sensor is built as a standalone fiber optic device 500 contained within a biocompatible metallic rod 502. The rod 502 contains two optical fibers 504, 506 (single- or multimode) along its axial direction. One fiber serves to bring the excitation light within the tissues while the other captures the back-scattered light. Fibers 504, 506 run parallel to each other and are separated by an adequate distance (1-2 mm) to fit into the hole bored by the dental drill bit (typ. 2 mm dia.). The skilled addressee will appreciate that the separation between the two fibers 504, 506 should be as large as possible to maximize penetration depth. Indeed, in back-reflected diffuse optical sensing, the depth of penetration is increased with source-detector separation. The skilled addressee will also appreciate that multimode fibers may be employed to increase light throughput in both channels. In this embodiment, the fiber probe itself is connected to the device back-end. As previously mentioned, the excitation fiber is connected to a light source (either LED, laser or other source) or multiple light sources each having an appropriate wavelength for optimized absorption by blood chromophores (mainly oxy- and deoxyhemoglobin). Typical wavelengths are around 660 nm and 850 nm. The light source output could be modulated at a reference frequency in the kHz range. The collection fiber is connected to an appropriate light detector such as a photodiode, an avalanche photodiode (APD), a photomultiplier tube (PMT), a camera or the like. The detector output signal is either AC-coupled or connected to a lock-in amplifier operating at the same reference frequency as the light source modulation. The goal of the modulation signal or the AC-coupling is to reject background signals coming from other tissues than the flowing arterial blood. A variation of this embodiment makes use of a varying input optical power into the tissue to establish the neurovascular bundle position relative to the probe based on an intensity threshold approach, where larger input powers will statistically increase linearly the number of photons reaching larger depths, thus improving the chance of detecting some of these photons that might probe the neurovascular bundle.

Standalone Self-Contained Low Coherence Interferometry-Based Fiber-Probe:

FIG. 10B shows another embodiment similar to the one shown in FIG. 10A in shape but implementing the OCT approach. As illustrated, a single fiber 508 can be used for illumination and collection purposes. Due to the difference in requirements between OCT and the spectral absorption concept, the fiber probe should be made of one or multiple single-mode optical fibers to prevent detrimental dispersion and spatial propagation modes mixing, according to one embodiment. The back-end of the probe utilizes classical OCT configurations, such as time-domain-based, frequency-domain OCT or swept-source-based implementations, as previously detailed. In this embodiment, the back-end is entirely fiberized and uses fiber couplers to connect with the probe itself, as is well-known in the art. In a further embodiment, the probe forward-looking configuration can be implemented for B-mode scanning, by integrating a proximal scanning system installed in the back-end coupled to a bundle of single mode optical fibers, or through a distal scanning mechanism integrated into the probe head itself that would use one single-mode optical fiber.

Drill-Integrated Probe:

Referring again to FIG. 6, any of the described embodiments can be integrated at the center of the drill bit 610 of a dental surgery drill. The center of a dental drill bit 610 can have a hollow core 602 to allow for cooling water to circulate down to the drilling site 604. The fiber probe can be inserted within this hollow core 602.

Combined OCT/Spectral Absorption Probe:

Such a combined configuration uses the advantages of each approach. The spectral absorption approach has potentially a greater detection range, while the OCT approach is more straightforward and offer potentially better resolution at short range. A combined sensor probe could thus potentially identify roughly the position of the IAN bundle at a distance with the spectral absorption mode and then switch to an OCT approach when close to the IAN (typ. within 1.5 mm). The sensor construction would require two or three optical fibers grouped in a bundle. A single-mode fiber would bring the excitation light. A second single-mode fiber would be used for OCT light collection, while a third multimode fiber would be used for the spectral absorption mode light collection channel. Alternatively, the single-mode excitation fiber could double-up as the collection fiber for the OCT technique.

Figure 11:
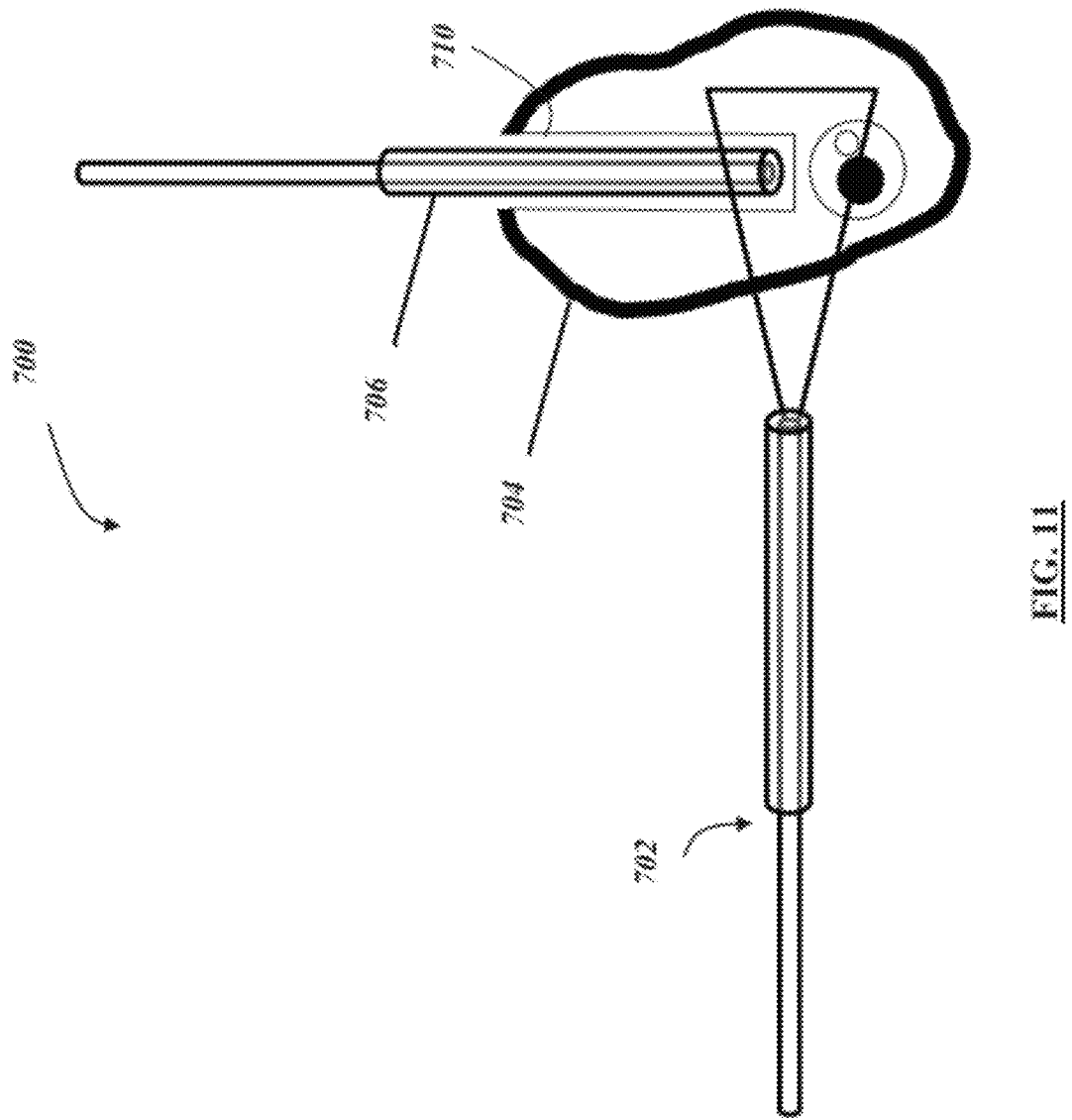
FIG. 11 is a schematics showing a disjointed spectral absorption IAN sensor configuration, according to one embodiment.

Spectral Absorption Fiber Probe with Disjointed Source and Collection Channels:

FIG. 11 shows an embodiment of a disjointed spectral absorption IAN sensor 700. In this configuration of the spectral absorption technique, one or multiple excitation optical fibers 702 are positioned on the side of the gum or jawbone 704, outside of the probe handpiece 706 itself (or the drill bit), while the detection optical fiber 708 is still integrated in the probe handpiece 706, within the drilling hole 710 in the bone 704. Such a configuration allows larger separation of the source and collection channels, which will increase depth sensitivity of the technique. Indeed, as previously mentioned, in back-reflected diffuse optical sensing, the depth of penetration is increased with source-detector separation. Alternatively, the source and collection channels can be reversed, with the detection being done laterally on the gum and the illumination being integrated in the drill bit, or probe handpiece. In a further embodiment, using multiple optical fibers built in a linear array may provide refined measurements of the neurovascular bundle's position in the jaw.

Figure 12:
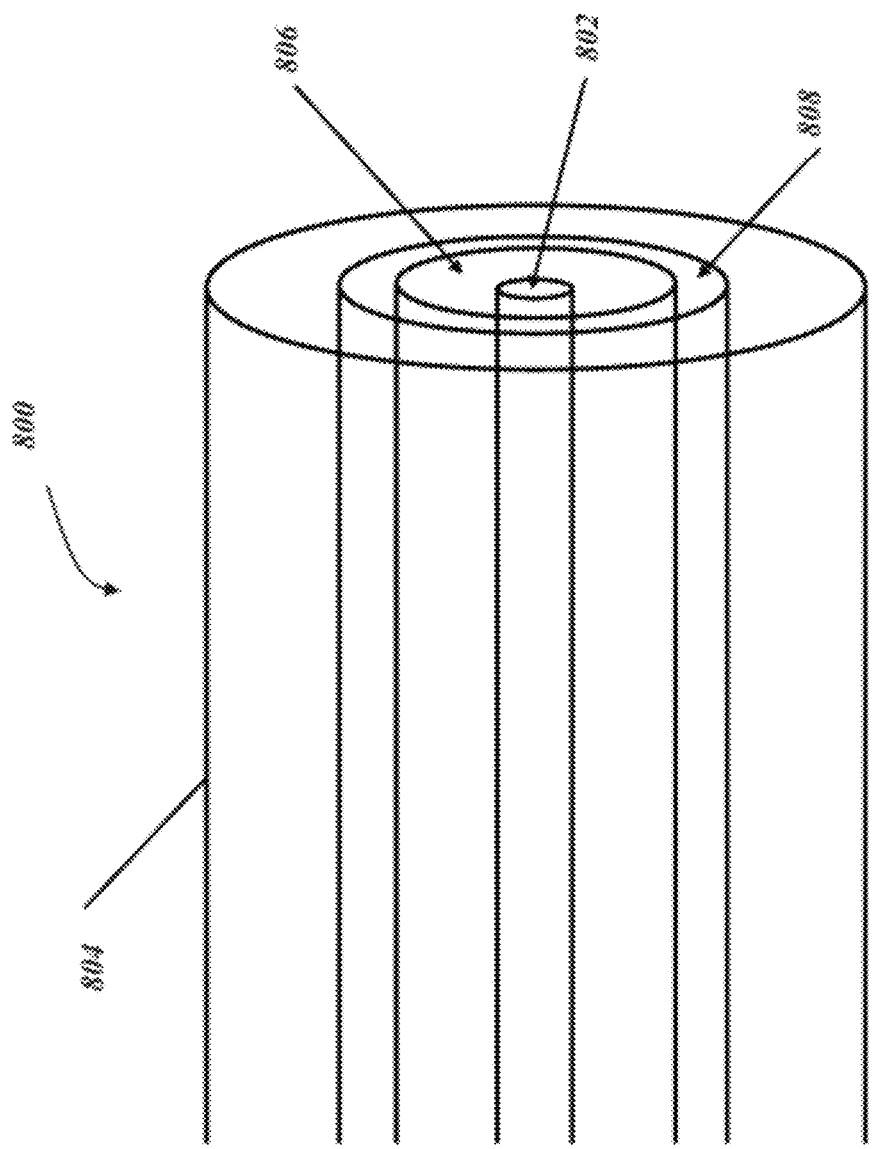
FIG. 12 is a diagram of a double-clad optical fiber-based IAN sensor handpiece design, according to one embodiment.

Use of a Double-Clad Optical Fiber:

FIG. 12 illustrates a double-clad optical fiber-based IAN sensor handpiece 800 which may be used alternatively to the use of two optical fibers in the probe. The core 802 of the double-clad optical fiber 804 is used as the excitation channel to send light into tissues and the first cladding 806 acts as the collection channel. In the OCT approach and in one embodiment, the core 802 is built for single mode propagation. The first clad 806 will typically have a large numerical aperture, making it ideal for light collection. The second clad 808 insure proper waveguide behavior for the first clad 806. This approach would benefit especially the OCT technique as the separation between core and first cladding would probably be too low for efficient implementation of the spectral absorption technique.

Figure 13:
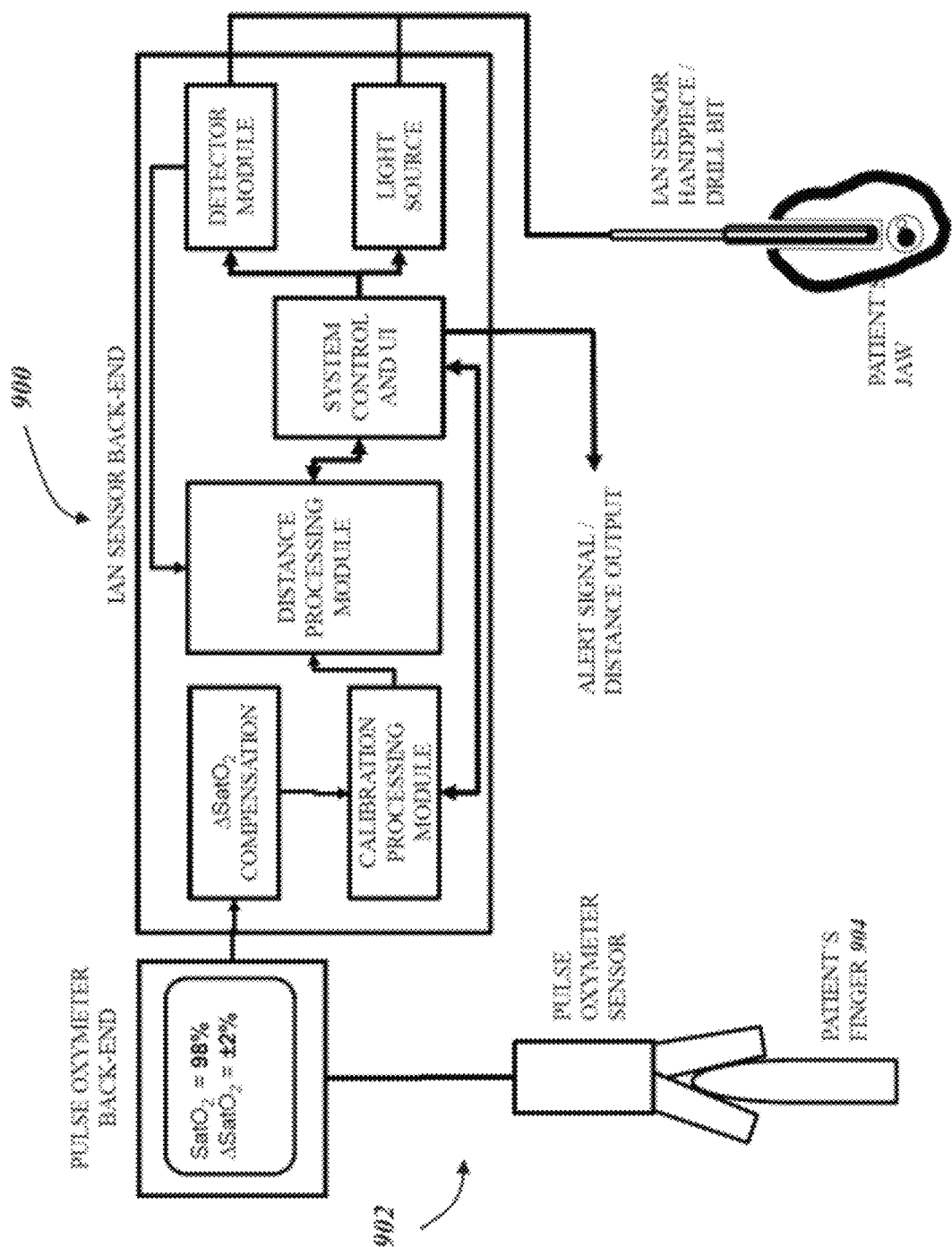
FIG. 13 is a diagram of a spectral absorption-based IAN sensor apparatus where a pulse oxymeter is used, according to one embodiment.

Combining the Spectral Absorption Probe with a Pulse Oxymeter in the Technique:

FIG. 13 shows a spectral absorption-based IAN sensor apparatus 900 that uses an entirely separate pulse oxymeter 902 operatively connected to a finger 904 of the patient as a monitor of blood oxygenation variations over the course of the drilling procedure, to maintain an inline calibration of the arterial blood absorption properties. In other words, this embodiment enables to compensate variations of blood optical properties from the oxygenation levels variation ($\Delta SatO2$) to provide more accurate distance measurements, by updating the device calibration factors in real-time. Indeed, large variations in the optical properties will skew the sensor distance measurement. That being said, normal individuals will generally not see variations in blood oxygenation larger than ~2%, which might well be within the error bar of the distance measurement.

Figure 14:
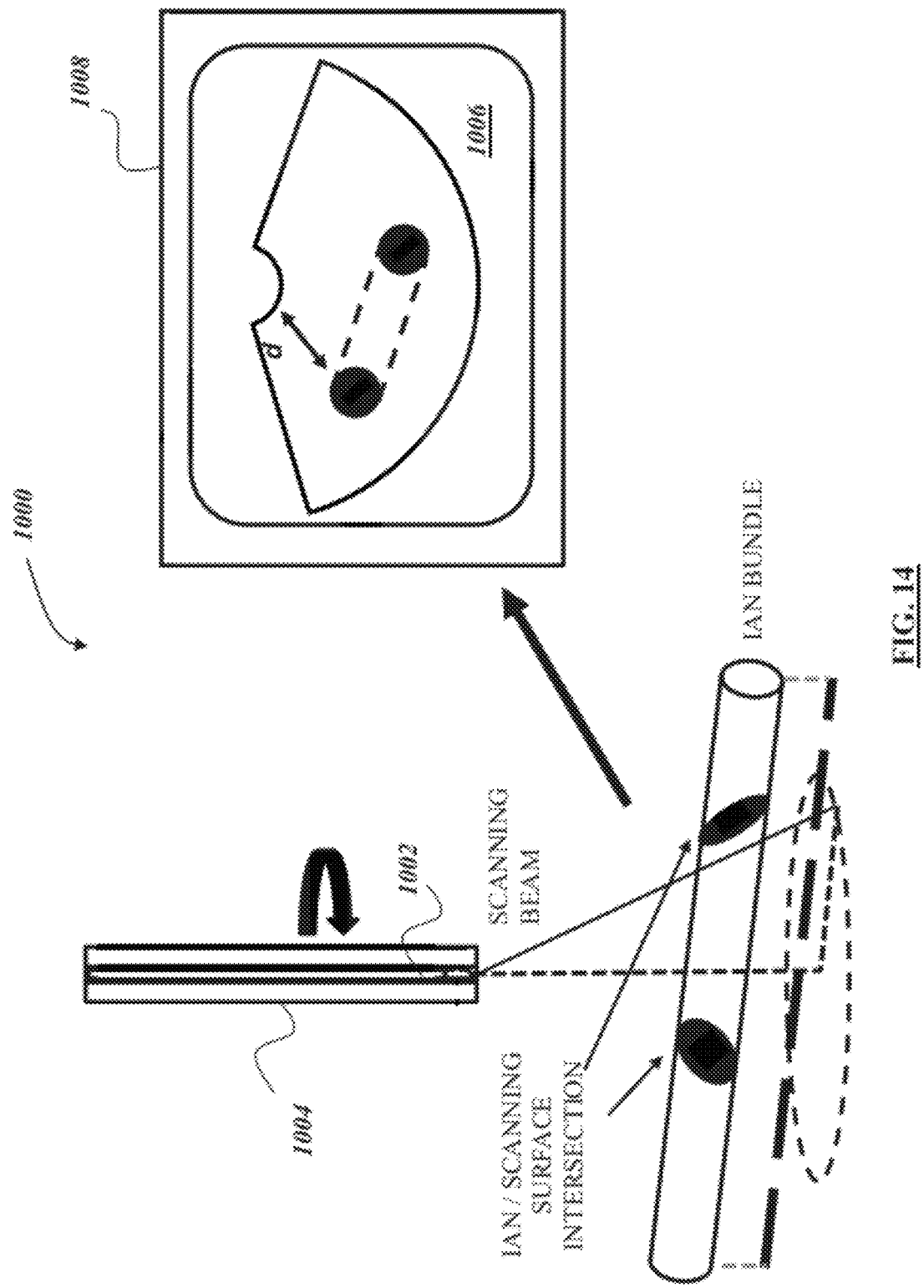
FIG. 14 is a schematics of another IAN sensor using a conical scanning principle, according to another embodiment.

Developing a B-Mode OCT Technique Using the Drill Rotation for Scanning:

FIG. 14 shows a IAN sensor 1000 using a conical scanning principle that uses the drill rotation and a beveled double-clad optical waveguide 1002 that rotates with the drill 1004 in such a way that the source and collection channels would observe the tissues in front of the drill tip slightly off-axis. As it should become apparent to the skilled addressee, this is an alternative implementation to the standard B-mode scanning technique that operates along a line in the transverse plane. The drill rotation would allow a ring in the transverse plane to be scanned along the light propagation axis, essentially probing a conical surface within the jaw. The IAN bundle would intersect this conical surface at two opposite locations. The signal processor (not shown) of the device 1000 could then create an image 1006 by "unfolding" the conical surface on a computer screen 1008, giving the dental surgeon a high resolution image similar to an ultrasonogram in real-time. The advantage of this B-mode scanning method is that the IAN bundle orientation in the transverse plane relative to the drill axis can be arbitrary. In the other implementations described, the IAN bundle should lie on the drilling axis, or the axis of the forward looking probe, to be detected properly. Otherwise the drill bit might pass beside the nerve and still produce damage, because the sensor did not "see" the IAN bundle. Note that with the NIR spectral absorption technique, this flaw is fairly reduced due to the volume averaging effect mentioned earlier.

Implement Doppler OCT in the Probe and Use Tissue Changes or Movement as a Contrast Mechanism:

In addition to using standard OCT in the sensor, this configuration uses the Doppler effect to lock on blood flow. Doppler OCT is generally used to measure quantitatively microvasculature blood flow. In the case of this sensor, a qualitative measurement is enough to locate the IAN bundle. As such, the implementation of Doppler measurements in the OCT device would be simpler and cheaper. Experiments were conducted with Doppler OCT on an ex vivo human jawbone piece from which the neurovascular bundle was removed and a tube containing a flowing scattering fluid was connected, imitating blood flow in the canal. Results have shown that using the Doppler Effect as part of the spectral absorption technique might benefit the device.

According to another embodiment, another variant of OCT data processing that utilizes changes or movement in the tissue like Doppler OCT, namely speckle variance OCT [Refs: A. Mariampillai et al., Opt. Lett. 33(13), 1530 (2008); A. Mariampillai et al., Opt. Lett. 35(8), 1257 (2010)], can be used to embody the sensor. It proceeds as follow: first, a series of B-mode images of the same sample section over time is acquired. Second, for each pixel location the average value and variance are computed using pixel value of all images at that same exact location. This process leads to two 2D images. The first one is made with the pixel average value. Therefore, non-zero pixels in that image are those associated with a stationary/non-moving part of the sample. The second image is made with the pixel variance values. Thus, non-zero pixels in that image are associated with the moving/spatially-varying part of the sample. In a similar fashion to Doppler OCT, this kind of processing will lead to contrast generation between hard and soft tissues in movement, or contrast based on tissue "viscosity". Results have shown that the fluid may be identified from the variance image, contrasting with the bone section. This method could potentially make good usage of blood flow in the neurovascular bundle.

Use of a Non-Specific Vascular Contrast Agent to Facilitate Artery Detection:

A vascular contrast agent, such as Indocyanine Green which is a NIR fluorescent dye approved for clinical use in a number of indications, can be used to enhance the signal coming from the artery in the IAN bundle. Injection of a bolus of ICG into the systemic circulation will momentarily make the artery in the IAN bundle fluoresce at 830 nm (when excited at 780 nm) against a non-fluorescent background, increasing the overall contrast dramatically. If tuned to the fluorescent wavelength, the spectral absorption sensor technique will have a much easier time at spotting the IAN bundle. The modulated excitation would equally translate to a modulated fluorescence signal. A difficulty is however that the device needs to be calibrated at two wavelengths (780 and 830 nm) instead of one. This can be solved by adding a second light source and operating in the same manner as described above for calibration at the two wavelengths, before the ICG injection.

In similar fashion, the various embodiments based on LCI/OCT can benefit from the potential application of optical clearing agents at the site of probing. Biocompatible optical clearing agents, such as fructose, glycerol, propylene glycol, glucose or mannitol solutions can partially replace the interstitial fluid due to hyperosmotic properties and provide a refractive index matching medium that reduces scattering due to a number of cell structures and organelles, thus increasing the transparency of the tissues to optical wavelengths and improving the depth penetration.

Dental Drill Integration of the Optical IAN Sensor

Integration of the sensor into a drill bit presents a number of mechanical challenges, the most important ones being the rotation speed and how to protect the optical sensor at the drill tip, without blocking light injection and detection. Dental drills can rotate at rates up to 20,000 RPM. In typical use for dental implant surgery, the rotation speed will be in the range of 2,000 to 4,000 RPM.

To fit within the hollow core of a drill bit, the optical fiber assembly should be secured in such a way that the optical fibers do not come into contact with the rotating inner wall. The friction at high rotating speeds would most certainly break the optical fibers. An alternative is to have the fiber assembly rotate with the drill bit, so that relative positioning of the fibers and the inner wall is stationary. FIG. 15A shows a drill-integrated IAN sensor 1100 rotating with the drill bit 1102 and using an optical fiber rotary joint 1104 for coupling the optical fibers in the drill head.

Figure 15B:
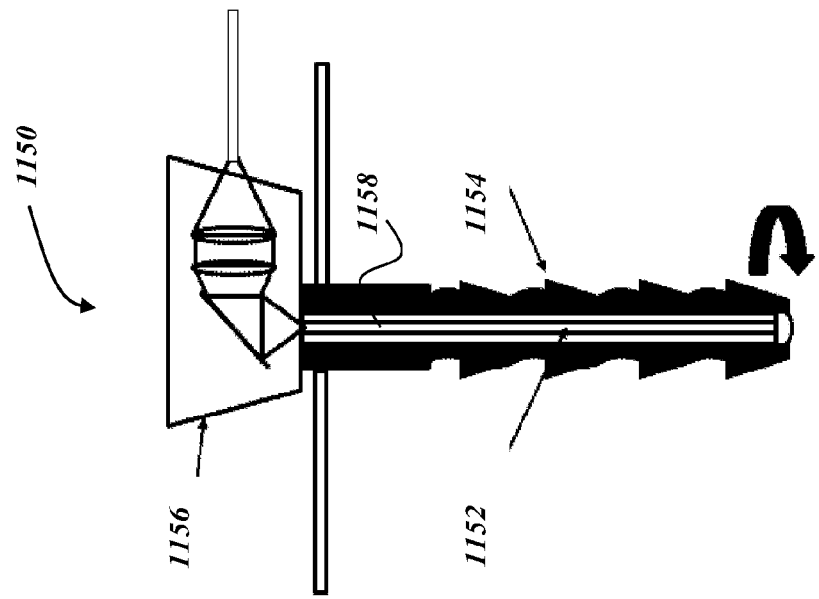
FIG. 15B is a diagram of a drill-integrated IAN sensor using a non-contact optical coupling, according to another embodiment.
Figure 15A:
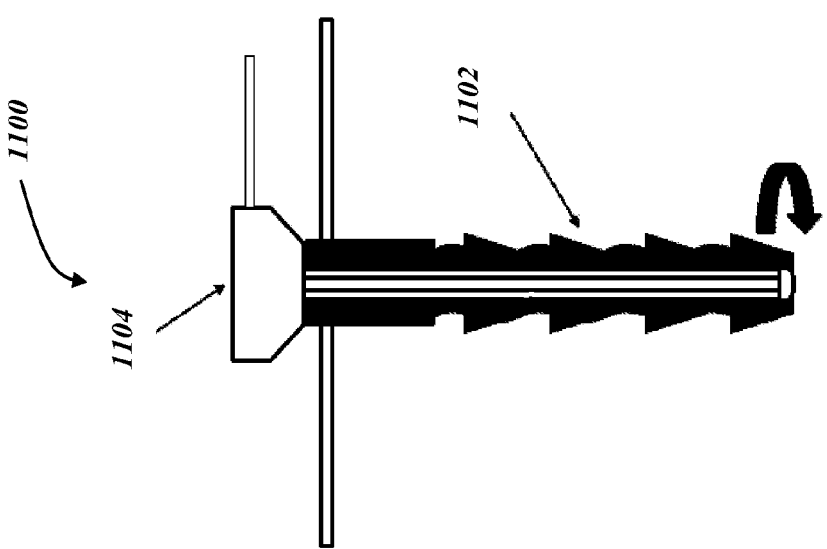
FIG. 15A is a diagram of a drill-integrated IAN sensor using an optical fiber rotary joint, according to one embodiment.

FIG. 15B illustrates another alternative drill integrated IAN sensor 1150 wherein a rod-like optical waveguide 1152 is built as an integral part of the drill bit 1154 with a non-contact optical coupler 1156 from the optical fibers 1158 coming from the back-end in the drill head. The skilled addressee will note that having a rotating handpiece requires that the probe design have circular symmetry, which is not achievable with a two-fiber design as the one shown in FIG.

10A. In this last case, the handpiece should remain stationary with the drill bit rotating around the sensing assembly, as previously detailed.

In a further embodiment, in order to prevent introduction of organic tissues and debris within the hollow core that could clog it and prevent proper function of the sensor, the tip of the drill bit may be plugged with a hard and transparent material (not shown), so it can withstand the large frictions of the drilling process while allowing light to pass through. Diamond or zirconium crystals would potentially be the best materials, due to their exceptional hardness and transparency in the visible and NIR spectral window but the skilled addressee will appreciate that other arrangements may be considered.

Extensions of the Technology to Other Applications

The described invention could also be used in other fields of surgery where proximity to a neurovascular bundle embedded in hard tissues, such as bone, must be assessed during a surgical activity such as drilling or cutting. It can also be used to identify the presence of voids inside tissue structures, such as sinus cavities in the cranial anatomy, during drilling procedures. As another example of application, a LCI/OCT-based probe could also be envisioned as a bone mapping tool in oral surgery to determine the gums thickness at specific locations, as long as the device detection range is sufficient.

The embodiments described above are intended to be exemplary only. The scope of the invention is therefore intended to be limited solely by the appended claims.

We claim:

1. A spectral absorption probe system for determining a distance between a tissue layer including an artery and a surgical drill tip during a procedure, comprising:
  a light source of the spectral absorption probe system for generating excitation light having a wavelength configured for absorption by blood chromophores;
  an excitation optical channel of the spectral absorption probe system to bring said excitation light near the tissue layer and the artery;
  a collection optical channel of the spectral absorption probe system, distinct from said excitation optical channel, for capturing diffused back-scattered light from said tissue layer and the artery, where said diffused back-scattered light is modulated by blood flow dynamics in said artery, said blood flow dynamics being a periodic change in blood volume in said artery due to a cardiac cycle;
  a light detector of the spectral absorption probe system operatively connected to said collection optical channel for detecting said diffused back-scattered light modulated by blood flow dynamics and for generating an oscillating signal, a frequency of said oscillating signal being related to said periodic change; and
  a signal processor of the spectral absorption probe system operatively connected to said light detector for determining the distance between the tissue layer including the artery and the surgical drill tip based on said back-scattered light using an amplitude of said oscillating signal and a value for surrounding tissue attenuation coefficient;
  wherein at least one of the excitation optical channel and the collection optical channel is included in an optical fiber and the optical fiber is integrated within a hollow core of a surgical drill bit including the surgical drill tip.

2. The spectral absorption probe system as claimed in claim 1, further comprising a biocompatible metallic rod surrounding said excitation optical channel and said collection optical channel.

3. The spectral absorption probe system as claimed in claim 1, wherein said excitation optical channel and said collection optical channel are each provided in a single double-clad optical fiber with a fiber core of said double-clad optical fiber bringing said excitation light near said tissue layer and a first clad of said double-clad optical fiber capturing said back-scattered light from said tissue layer.

4. The spectral absorption probe system as claimed in claim 1, wherein said signal processor is further configured to determine said distance to said tissue layer between 1 mm and 5 mm.

5. The spectral absorption probe system as claimed in claim 1, wherein the light source is selected from a group consisting of a LED, a laser and a set of light source units.

6. The spectral absorption probe system as claimed in claim 1, wherein the wavelength of the light source is comprised between 650 nm and 900 nm.

7. The spectral absorption probe system as claimed in claim 1, further comprising an additional light source having a wavelength configured for absorption by blood chromophores, the wavelengths of the light source and of the additional light source being each comprised between 650 nm and 900 nm.

8. The spectral absorption probe system as claimed in claim 1, wherein the light detector is selected from a group consisting of a photodiode, an avalanche photodiode (APD), a photomultiplier tube (PMT) and a camera.

9. The spectral absorption probe system as claimed in claim 1, further comprising a calibration unit having a pulse oxymeter for monitoring oxygen saturation levels to maintain an inline calibration of arterial blood absorption properties.

10. The spectral absorption probe system as claimed in claim 1, wherein said signal processor is further configured to determine said surrounding tissue attenuation coefficient that is determined according to absorption and scattering in surrounding tissue of a calibration excitation signal.

11. The spectral absorption probe system as claimed in claim 1, wherein the signal processor comprises a lock-in amplifier and a heterodyning processing circuit connected thereto.

12. The spectral absorption probe system as claimed in claim 1, wherein the light detector is alternating current (AC) coupled to the signal processor.

13. A combined spectral absorption and low coherence interferometry probe system for determining a distance between to a tissue layer including an artery and a surgical drill tip during a procedure, comprising:
  a light source of the combined spectral absorption and low coherence interferometry probe system for generating excitation light having at least one wavelength configured for absorption by blood chromophores and low coherence;
  an excitation optical channel of the combined spectral absorption and low coherence interferometry probe system to bring said excitation light near the tissue layer and the artery;
  a first collection optical channel of the combined spectral absorption and low coherence interferometry probe system, distinct from said excitation optical channel, for capturing diffused back-scattered light from said tissue layer and the artery, where said diffused back-scattered light is modulated by blood flow dynamics in said artery, said blood flow dynamics being a periodic change in blood volume in said artery due to a cardiac cycle;
  a first light detector of the combined spectral absorption and low coherence interferometry probe system operatively connected to said first collection optical channel for detecting said diffused back-scattered light modulated by blood flow dynamics and for generating an oscillating signal, a frequency of said oscillating signal being related to said periodic change;

a first digital signal processor of the combined spectral absorption and low coherence interferometry probe system operatively connected to said first light detector for determining the distance between the tissue layer and the surgical drill tip based on said diffused back-scattered light using an amplitude of said oscillating signal and a value for surrounding tissue attenuation coefficient;

a low coherence interferometry sub-system of the combined spectral absorption and low coherence interferometry probe system operatively connected to the excitation optical channel;

including a second collection optical channel, distinct from said first collection optical channel, for capturing low-coherence back-scattered light from said tissue layer and the artery, a beam splitter, a reference mirror and a second light detector, distinct from said first light detector, operatively connected to said second collection optical channel;

a second signal processor operatively connected to said low coherence interferometry subsystem for determinant the evaluating a distance between said tissue layer including the artery and the surgical drill tip based on said low-coherence back-scattered light received by said second collection optical channel, said first digital signal processor and said second signal processor being provided by one of distinct processors and a common processor;

wherein at least one of the excitation optical channel and the collection optical channel is included in an optical fiber and the optical fiber is integrated within a hollow core of a surgical drill bit including the surgical drill tip.

14. The combined spectral absorption and low coherence interferometry probe system as claimed in claim 13, wherein the excitation optical channel is provided by a first single mode fiber and further wherein the second collection optical channel is provided by a second single mode fiber for OCT mode light collection and wherein the first collection optical channel is provided by a multimode fiber for spectral absorption mode light collection.

15. The combined spectral absorption and low coherence interferometry probe system as claimed in claim 13, further comprising a forward-looking transverse scanner enabling B-mode imaging.

16. The combined spectral absorption and low coherence interferometry probe system as claimed in claim 13, wherein the excitation optical channel and the second collection optical channel are each provided by a single fiber.

17. A spectral absorption method for determining a distance between a tissue layer including an artery and a surgical drill tip during a procedure, comprising:

generating an excitation light by a light source of a spectral absorption probe system having a wavelength configured for absorption by blood chromophores;

bringing said excitation light by an excitation channel of the spectral absorption probe system near the tissue layer and the artery;

capturing by a collection channel of the spectral absorption probe system diffused back-scattered light from said tissue layer and the artery, where said diffused back-scattered light is modulated by blood flow dynamics in said artery, said blood flow dynamics being a periodic change in blood volume in said artery due to a cardiac cycle;

detecting by a light detector of the spectral absorption probe system said diffused back-scattered light modulated by said blood flow dynamics;

generating by the spectral absorption probe system an oscillating signal, a frequency of said oscillating signal being related to said periodic change; and processing by a signal processor of the spectral absorption probe system said diffused back scattered light from said tissue layer and the artery for determining the distance between the tissue layer including the artery and the surgical drill tip, said processing including using an amplitude of said oscillating signal and a value for surrounding tissue attenuation coefficient, wherein at least one of the excitation optical channel and the collection optical channel is included in an optical fiber and the optical fiber is integrated within a hollow core of a surgical drill bit including the surgical drill tip.

18. The spectral absorption method as claimed in claim 17 further comprising evaluating proximity to an inferior alveolar nerve in situ, said tissue layer including said inferior alveolar nerve.

19. The spectral absorption method as claimed in claim 17, further comprising monitoring oxygen saturation levels to maintain an inline calibration of arterial blood absorption properties.

20. The spectral absorption method as claimed in claim 17, further comprising determining said surrounding tissue attenuation coefficient according to absorption and scattering in surrounding tissue of a calibration excitation signal.

21. The spectral absorption method as claimed in claim 17, wherein said diffused back-scattered light is captured angularly and at a given distance with respect to said brought excitation light.

22. The spectral absorption method as claimed in claim 17, further comprising using a vascular contrast agent.

23. A combined spectral absorption and low coherence interferometry method for determining a distance between a tissue layer including an artery and a surgical drill tip during a procedure, comprising:

generating by a light source of the combined spectral absorption and low coherence interferometry probe system an excitation light having at least one wavelength configured for absorption by blood chromophores and low coherence;

bringing said excitation light by an excitation optical channel of the combined spectral absorption and low coherence interferometry probe system near the tissue layer and the artery;

capturing by a first collection optical channel of the combined spectral absorption and low coherence interferometry probe system diffused back-scattered light from said tissue layer and the artery, where said diffused back-scattered light is modulated by blood flow dynamics in said artery, said blood flow dynamics being a periodic change in blood volume in said artery due to a cardiac cycle;

detecting by a first light detector of the combined spectral absorption and low coherence interferometry probe system said diffused back-scattered light modulated by blood flow dynamics;

generating by a digital signal processor of the combined spectral absorption and low coherence interferometry probe system an oscillating signal, a frequency of said oscillating signal being related to said periodic change;

processing by the digital signal processor said diffused back-scattered light for determining a first distance between the tissue layer including the artery and the surgical drill tip, said determining said distance including using an amplitude of said oscillating signal and a value for surrounding tissue attenuation coefficient;

capturing by a low coherence interferometry sub-system of the combined spectral absorption and low coherence interferometry probe system low-coherence back-scattered light from said tissue layer and the artery;

performing by the low coherence interferometry sub-system interferometry between said excitation light and said low-coherence back-scattered light for providing an interference signal; and processing by the digital signal processor said interference signal for determining a second distance between the tissue layer including the artery and the surgical drill tip wherein at least one of the excitation optical channel and the collection optical channel is included in an optical fiber and the optical fiber is integrated within a hollow core of a surgical drill bit including the surgical drill tip.

* * * * *

UNITED STATES PATENT AND TRADEMARK OFFICE
CERTIFICATE OF CORRECTION

| | |
|---|---|
| PATENT NO. | : 9,179,843 B2 |
| APPLICATION NO. | : 13/329557 |
| DATED | : November 10, 2015 |
| INVENTOR(S) | : Hassan Ghaderi Moghaddam et al. |

It is certified that error appears in the above-identified patent and that said Letters Patent is hereby corrected as shown below:

IN THE CLAIMS:

In Column 18, line 46 (within Claim 13), please change "between to a tissue layer including an artery and a surgical" to -- between a tissue layer including an artery and a surgical --

In Column 19, Lines 27 and 28 (within Claim 13), please change "low coherence interferometry subsystem for determinant the evaluating a distance between said tissue layer" to -- low coherence interferometry subsystem for evaluating a distance between said tissue layer --

Signed and Sealed this
Fourteenth Day of June, 2016

Michelle K. Lee
*Director of the United States Patent and Trademark Office*